United States Patent [19]

de Zabala et al.

[11] 4,385,115
[45] May 24, 1983

[54] DIAGNOSTICS TESTING DEVICES AND PROCESSES

[75] Inventors: Edward F. de Zabala, Pequannock; Edward V. Savard, Mahwah; Doris B. Taylor, Parsippany, all of N.J.

[73] Assignee: Hoffmann-La Roche Inc., Nutley, N.J.

[21] Appl. No.: 199,399

[22] Filed: Oct. 22, 1980

[51] Int. Cl.³ .................. C12Q 1/20; C12Q 1/18; C12M 1/16; C12M 1/18
[52] U.S. Cl. .................... 435/33; 222/486; 222/565; 422/64; 435/32; 435/299; 435/300; 435/301
[58] Field of Search ............ 435/32, 33, 299, 300, 435/301; 222/485, 486, 565

[56] References Cited

U.S. PATENT DOCUMENTS

| 3,083,145 | 3/1963 | Ryan | 435/300 X |
|---|---|---|---|
| 3,367,841 | 2/1968 | Buissiere et al. | 435/287 X |
| 3,416,998 | 12/1968 | Streitfeld | 435/34 X |
| 3,692,488 | 9/1972 | Schwartz | 435/301 X |
| 3,740,196 | 6/1973 | Stroterhoff | 422/61 |
| 3,827,943 | 8/1974 | Mann | 435/312 X |
| 3,893,891 | 7/1975 | Tannenbaum et al. | 435/289 |
| 3,895,661 | 7/1975 | Praglin et al. | 435/293 X |
| 3,901,658 | 8/1975 | Burtis et al. | 422/72 |
| 3,902,852 | 9/1975 | Lemieux et al. | 422/70 |
| 3,912,456 | 10/1975 | Young | 422/64 |
| 3,912,596 | 10/1975 | Haque et al. | 435/301 X |
| 4,018,652 | 4/1977 | Lanham et al. | 435/287 X |
| 4,070,249 | 1/1978 | Janin et al. | 435/300 X |
| 4,073,693 | 2/1978 | Janin | 435/300 X |
| 4,076,592 | 2/1978 | Bradley | 435/301 X |
| 4,129,419 | 12/1978 | Hermann, Jr. | 422/64 |
| 4,129,483 | 12/1978 | Bochner | 435/301 X |
| 4,148,689 | 4/1979 | Hino et al. | 435/182 |
| 4,154,793 | 5/1979 | Guizan | 435/310 X |
| 4,237,234 | 12/1980 | Meunier | 435/301 |
| 4,239,853 | 12/1980 | Bradley | 435/301 X |
| 4,260,687 | 4/1981 | Jacobson et al. | 435/300 X |

Primary Examiner—Robert J. Warden
Attorney, Agent, or Firm—Jon S. Saxe; George M. Gould; Steve T. Zelson

[57] ABSTRACT

A convenient, self-contained, disposable device suitable for the rapid identification of microorganisms, having capability for simultaneously carrying out a multiplicity of analytical determinations. The device comprises a disc-shaped arrangement defining a multiplicity of satellite testing chambers each of which is connected to a centrally defined chamber. The central chamber is provided with a movable sleeve or piston arrangement. Liquid sample is received in the central chamber and the sleeve is manipulated to provide samples uniformly and simultaneously to each of the satellite testing chambers without resorting to external means, such as positive or a negative pressurization or centrifugal force. Also disclosed are unique disc-shaped optically transparent support films which are coated on one or both sides with analytical substrates or reagents which are predispensed to the satellite testing chambers.

33 Claims, 13 Drawing Figures

DIAGNOSTICS TESTING DEVICES AND PROCESSES

BACKGROUND OF THE INVENTION

The present invention relates to diagnostic testing and more particularly to methods and structures for microorganism identification, wherein a disc-shaped device is provided having a central sample-dispensing chamber communicating with a multiplicity of circumferentially arranged analysis chambers.

Devices useful for the identification of microorganisms or other diagnostic assays requiring a substantially simultaneous multiplicity of determinations, are well-known in the art. Generally the means utilized for bringing samples into contact with substrates (i.e. substances which microbes can utilize or convert to another substance), reagents (i.e. an indicator, something added to a reaction mixture in order to detect the utilization or conversion of a substrate) or inhibitors and the like (or vise versa) fall into four categories: centrifugal force, aspiration/vacuum, positive pressure and gravity. It is common to employ more than one of these means in a single arrangement. The state of the art is exemplified in the following prior art, which individually and collectively demonstrates the previous requirements for complex support equipments and/or manipulations of the sample and/or testing substances.

U.S. Pat. No. 3,776,817 to von der Pfordten discloses a device useful for determining bacterial growth comprising a disc arrangement mounted for rotation, having a central cavity and four equi-spaced apart peripheral cavities. In contrast to the device of the present invention, as example, the peripheral cavities of the von der Pfordten device do not cummunicate with and accordingly are not loaded from the central cavity nor are means provided therefor. The central cavity in this device simultaneously contains both medium and sample, and unlike the present invention is utilized for control for comparative readings with the peripheral cavities.

U.S. Pat. No. 3,759,666 to Hill discloses a disc-shaped rotary device useful for performing a series of analytical determinations on a sample of body fluid. This device contains thirty analytical sites or stations each of which is comprised of a set of three specifically designed and inter-related cavities extending radially inwardly toward a central core area. In operation, one of the inward-most extending cavities for each site is loaded with reagent and the second with sample, only for every other site, thus giving a control for each of fifteen determinations. The reagent and samples, where they are present, are mixed and conveyed by centrifugal force to the outermost cavity for spectrophotometrical reading. Thus, there is, for example, no teaching of filling of the "sample analysis" cavities from a central chamber, by any means, and no teaching of pre-dispensed substances useful in the identification of microorganisms housed in the analysis cavities. Hill is typically representative of the rather large body of patents and published literature covering rotor arrangements in complex and expensive centrifugal analyzers.

U.S. Pat. No. 4,129,419 to Hermann discloses a disposable device for the simultaneous loading of approximately one-third of the receptacles radially arranged around a centrifugal analyzer head. The device comprises a rack holding a number of containers, e.g. test tubes, containing a fluid to be dispensed in equal volumes to compartments in the centrifugal analyzer. In operation, the rack is adjusted to a horizontal orientation and a metered amount of gas under pressure injected into the assembly. The amount of fluid entering each compartment of the analyzer by gravitational flow is thereby controlled by equalization of the pressure within the rack. This assembly inter alia operates on a different principle than the device of the present invention which is concerned for example with simultaneously providing equal quantities of a test sample from a central chamber to peripheral testing chambers.

U.S. Pat. No. 4,154,793 to Guigan discloses a device for conditioning a liquid sample for analysis comprising a disc-like assembly having a central receptacle and peripheral cells connected to the central receptacle by ducts. Each of the cells is characterized by having its inlet for the liquid from the central receptacle proximate its radially outermost surface from the central receptacle and an outlet for escaping air on its radially innermost surface. The disclosed device also differs from the present invention, for example, in that sample from the central receptacle is transferred to the peripheral cavities only through the use of centrifugal force, and the arrangement does not provide for predispensed substances housed in the peripheral cells.

U.S. Pat. No. 3,912,596 to Hague, et. al. discloses a culture disc having radially arranged dividers which extend inwardly from the periphery to define a partially compartmentalized structure with a common central area, which enables the filling of all compartments defined by the dividers simultaneously with a liquid, solidifiable culture medium initially deposited at the central area. By means of a disc having needle-like possessions aligning with wells in a second disc containing sample, the compartments containing solidified medium can be simultaneously innoculated with sample for culture growth. The disclosed assembly is totally different from that of the present invention wherein individual chambers containing different types of media are simultaneously innoculated from a central cavity containing sample.

U.S. Pat. No. 3,912,456 to Young discloses an analytical assembly having a large number of receptacles for receiving specimens and/or reagents from a rotatably mounted aspirator and dispenser arm arrangement. There is, for example, no teaching of a compact disc-shaped device such as the present invention and no teaching of simultaneous innoculation of a multiplicity of peripheral test cavities with sample from a central chamber.

U.S. Pat. No. 3,827,943 to Mann discloses a culture vessel comprising a series of parallel culture tubes having a sealable of inlet/outlet opening at one end and a filter plate opening at the other, said openings being common to all tubes. The tubes are capable of being detached from a support mechanism and being rolled on free or driving wheels or rollers. The device is substantially different from the present invention.

U.S. Pat. No. 3,902,852 to Lemieux, et. al. discloses a mechanism whereby a multiplicity of samples is aspirated from respective sources and delivered to receptacles by a series of syringes. The disclosed mechanism provides for withdrawal of samples from the receptacles in like manner. Although the disclosed device provides for the simultaneous innoculation of a plurality of receptacles with sample via a single mechanical manipulation, the mechanism by which this is achieved is complex and totally different from and fails to respond to several elements of the present invention.

U.S. Pat. No. 3,901,658 to Burtis, et al. discloses a rotor device for separating whole blood and performing diagnostic tests on the plasma thereof. The plasma is provided in measured amounts to diagnostic reagent-containing peripheral chambers from a centrally located bowl. There is, however, neither teaching nor suggestion, for example, as to how the desired separation and analysis might be carried other than through the use of centrifugal force.

U.S. Pat. No. 3,893,891 to Tannenbaum, et al. discloses a diffusion chamber arrangement for growing microorganisms, having a number of organism-populated growth chambers each of which is demountable from a central diffusion reservoir containing a culture medium. The growth chambers are separated from the central reservoir by filters which permit passage of medium and metabolic products but no organisms, thereby retaining the purity of the culture growing within each growth chamber.

U.S. Pat. No. 3,692,488 to Schwartz discloses a device wherein test tubes are mounted in a circular base plate and attached to a central manifold. A flexible container holding reagent is compacted by means of a cam operated by a pump thereby expelling reagent into the manifold and thus into the test tubes. It is stated that the flexible supply container may be compressed by hand if the amount of reagent is relatively small and the exact quantity supplied is not critical. In contrast, the device of the present invention affords a simple and convenient means whereby an exact quantity of sample is uniformly dispensed to each of a series of chambers peripherally arranged about a central dispensing chamber by a single simple hand manipulation and without the need for external means such as a pumping device. The Schwartz arrangement thus fails to respond to several elements of the present invention.

U.S. Pat. No. 3,895,661 to Praglin, et al. discloses a device for determining susceptibility of an organism to a number of antibacteria agents, having a series of compartments arranged in a row which communicate with a common dispensing chamber structure and into which is placed a measured amount of bacterial innoculum and an antibiotic disc. This dispensing structure in turn is disposed to receive the contents of an externally supplied container which is mountable on the device. The contents of the container are emptied into the dispensing chamber by orienting the device via a 180¼ rotation to allow full-gravity flow. The device is then manipulated to yet another orientation (a 90¼ rotation) to allow gravity flow of the contents of the dispensing chamber into the series of compartments. Antibiotic discs are then separately loaded into the compartments by an elaborate mechanism. Inoculation apparently is carried out with the aid of vacuum conditions. This device, as example, fails to provide simultaneous introduction of a uniform amount of sample into the compartments.

U.S. Pat. No. 4,018,652 to Lanham, et al. discloses a culture medium arrangement for testing a sample of water for bacterial contamination. The disclosed device comprises a cassette having a number of chambers containing culture media with inlet and outlet channels. The inlet channels are connected to a needle-like projection which tightly fits into a tube holding the water specimen to be tested. The wells are filled by means of vacuum which pulls the air from the casette and bubbles it out through the specimen itself. The vacuum it released and the specimen then flows into the wells. There is no suggestion or means other than an externally applied vacuum by which the wells can be with loaded with specimen.

U.S. Pat. No. 3,740,196 to Stroterhoff discloses a device for chemical spot testing for the presence of mustard agents or nerve gas in the air. A device comprises a reaction well containing chemical inhibitors and at least one other compartment or well containing prepackaged reagent solutions, said compartment being connected to the reagent well by a channel. In use, the reaction well is exposed to the atmosphere and one or more agent solutions added thereto by manually rupturing the packages and causing the solutions to flow to the reagent well. This device is likewise clearly distinguishable from the device of the present invention.

With regard to the support films coated with analytical substrates or reagents as disclosed herein in accordance with the present invention, the following prior art is noted.

U.S. Pat. No. 4,148,689 to Hino, et al. discloses the immobilization of microorganisms having enzymatic activity in a hydrophilic complex gel. The disclosed gel comprises a homogeneous mixture of a water-soluble polymer, such as polyvinyl alcohol, gelatin or a cellulose derivative such as carboxymethylcellulose and a tetraalkoxysilane. The components of a gel are mixed to form a sol, with the desired microbial cells disbursed therein and a resulting mixture gelled under mild conditions. The desired "reagent" is disbursed throughout the resulting gel.

U.S. Pat. No. 3,367,841 to Buissiere, et al. discloses a device for studying living cells comprising in a suitable container a disc having impregnated therein a suitable reagent and color indicator means, the disc being placed on or in juxtaposition with a second larger disc free of the reagents. All of the first disc and a portion of the second disc are covered with a water-and-air-impermeable covering. In use, a specimen to be studied is applied to the exposed portion of the larger disc and, over a period of incubation, mixing of the reagent and sample occurs throughout by capillary action. Results are thereby obtained for both aerobic and non-aerobic conditions.

U.S. Pat. No. 3,416,998 to Streitfeld discloses agar sheets for detecting microorganisms. Each sheet contains disbursed throughout reagents necessary for detecting particular organisms. The sheets, labeled or cut into distinctive shapes are principally intended to be placed on nutrient medium innoculated with test organisms, thereby giving as many individual tests as the number of sheets utilized.

What the prior art particularly lacks is a small, hand-held, inexpensive, versatile and disposable device which possesses inter alia the following combined attributes:

(a) very simple to use;

(b) requires no significant preparation for use beyond the mere introduction of sample;

(c) requires no sterilization or special atmosphere;

(d) has virtually no limitations regarding shelf life and needs no refrigeration;

(e) needs no external equipment (e.g. centrifuges, vaccuum generators or pressure pumps), activating forces or complex manipulations, beyond a single, reversible, very brief, simple hand movement of a self-contained element; and (f) delivers with this singular movement a uniform amount of sample to each of the multiplicity of analysis locations virtually simultaneously.

Beyond these attributes, it is important that such a device be able to provide a large number of analysis locations (for a corresponding large number of tests), notwithstanding availability of only a small amount of sample (starting material), and still meet the uniform distribution requirement for all analysis locations, even if the device is not level when actuated.

SUMMARY OF THE INVENTION

It is a principle objective of this invention to provide a device which has all of the above attributes and meets the above criteria.

The task of providing such a device is solved in accordance with the invention with a disc-shaped structure having a central sample chamber which communicates with each of a circumferentially-arranged series of analysis chambers via means requiring only a single, reversible, simple hand movement for controlling the simultaneous uniform distribution of sample to the analysis chambers, and in which the analysis chambers are provided with pre-dispensed substances, such as reagents, in solid form which are useful in the diagnostic and identification processes of interest.

According to the broader device aspects of the present invention, there is provided a diagnostic device having a first chamber for receiving a sample and a multiplicity of analysis chambers having controlled communication with the first chamber, wherein the improvement comprises the combination of at least one diagnostically useful substance predispensed in each of the analysis chambers and a self-contained means for controlling communication between the first chamber and the analysis chambers, including means for dispensing sample from the first chamber virtually simultaneously and in uniform amount to each of the analysis chambers.

Also according to the broader aspects of the present invention, there is provided the combination comprising at least one substance useful in a predetermined diagnostic test of a sample, a support which is compatible with said substance and said sample, and a film-forming substance compatible with said substance, said sample and said support for enabling said substance to be coated onto at least one surface of said support in a final dry form.

According to the broader method aspects of the invention, there is provided a diagnostic method comprising pre-dispositing at least one selected substance useful in the identification of at least a part of a sample into each of a series of analysis chambers in solid form, depositing the sample in a single source chamber, and providing simultaneous access to each of the analysis chambers such that a uniform amount of sample is received therein.

Further in accordance with the broader method aspects of the invention, there is provided a method of fabricating a device useful in microorganism identification, comprising selecting at least one substance useful in the identification of microorganisms, selecting at least one film-forming substance which is compatible with each substance selected in the above step and also the microorganisms to be identified, making a film-forming solution by mixing the substances of the aforementioned first two steps, selecting an optically transparent support material which is compatible with the constituents of the above mixture and also the microorganisms to be identified, and applying the mixture to at least one surface of the support material so as effect a dry film thereon.

The invention is also concerned with the use of Mylar ® (polyester) and Petra ® (polyethene terephthalate) as compatible substrate support materials in connection with the identification of microorganisms.

The broader possibilities of use and application of devices constructed according to the present invention will be particularly appreciated since such a device obviates the need for skilled preparers and technicians, elaborate clinical or other testing facilities and their associated complex and expensive equipments, and the requirement for machine readability, although it is also a feature of devices constructed according to the present invention to be readily machine readable and actuable, if desired.

Such a device is reliably able to simultaneously provide to each analysis chamber a relatively very small amount (about 0.2 ml) of sample, from a very small starting sample volume of e.g. 3 ml or less, for say a sixteen-chamber device. In addition, it is not required that the device be kept level in order to meet the burden of uniform distribution to each analysis chamber.

In addition to the afore-mentioned attributes, the device made in accordance with the present invention possesses the following features and advantages:

(1) lends itself to micro-analytical procedures
(2) adaptable to a wide range of microbiological analyses, biochemical and immunological techniques and to rapid microbial susceptibility testing
(3) adaptable to chemical analysis, such as e.g. measurement of glucose, and enzematic analysis
(4) employable in both manual and automated testing proceedures
(5) readily compatible with programmed analysis for generating interpretive results
(6) provides for greatly reduced reaction times (e.g. 2–4 hrs.)

Such a device offers reagent/substrate stability in a dry form, with these substances being predispensed in proper quantities for conducting the tests of interest. Thus, the need for special storage conditions, such as refrigeration, is eliminated, as is the need for preparation of the substances and their introduction into the device. The substances to be used in diagnosing or identifying an unknown are provided in the device in such a way that incompatibles are separated and prevented from interaction until the time of actual use.

Unlike state-of-the art arrangements which measure growth and end products of growth of organisms, the present invention is able to provide reactions measuring endogeneous respiration or metabolic activity (i.e. the resting metabolism of the organism and its ability to utilize some substrate with the enzymes it has at that time), thus obviating the need for special conditions such as anerobic atmosphere or sterile conditions. The prior art arrangements generally are far from sensitive enough to measure substrate utilization within the short time period contemplated by this invention (2–4 hrs), since they require a substantial increase in population density by growth in order to use the substrate being tested to be able to detect that utilization. Prior to the present invention the alternative available comprised the use of very complex and expensive instrumentation to provide the sensitivity levels desired. In the present invention the highly controlled minute volumes in which the reactions are taking place, together with formulations on the discs enable such measurements to be performed inexpensively. An added benefit provided by the present invention is that since measurements are completed within 2-4 hrs, any bacterial contamination is minimal and would not practically affect the outcome of the test. Testing substances for diagnostic tests involving endogenous respiration of microorganisms can include carbohydrates, organic acids and compounds, amino acids, inorganic substrates and metabolic inhibitors.

BRIEF DESCRIPTION OF THE DRAWINGS

Other objects, features and advantages of the invention will become more apparent from the following description, given by way of illustration and taken in conjunction with the accompanying drawings, in which.

DESCRIPTION OF THE PREFERRED EMBODIMENTS

In the following description, it should be kept in mind that the figures illustrating the invention are not necessarily to scale and in some instances have been partially exaggerated for ease of understanding.

Figure 1A:
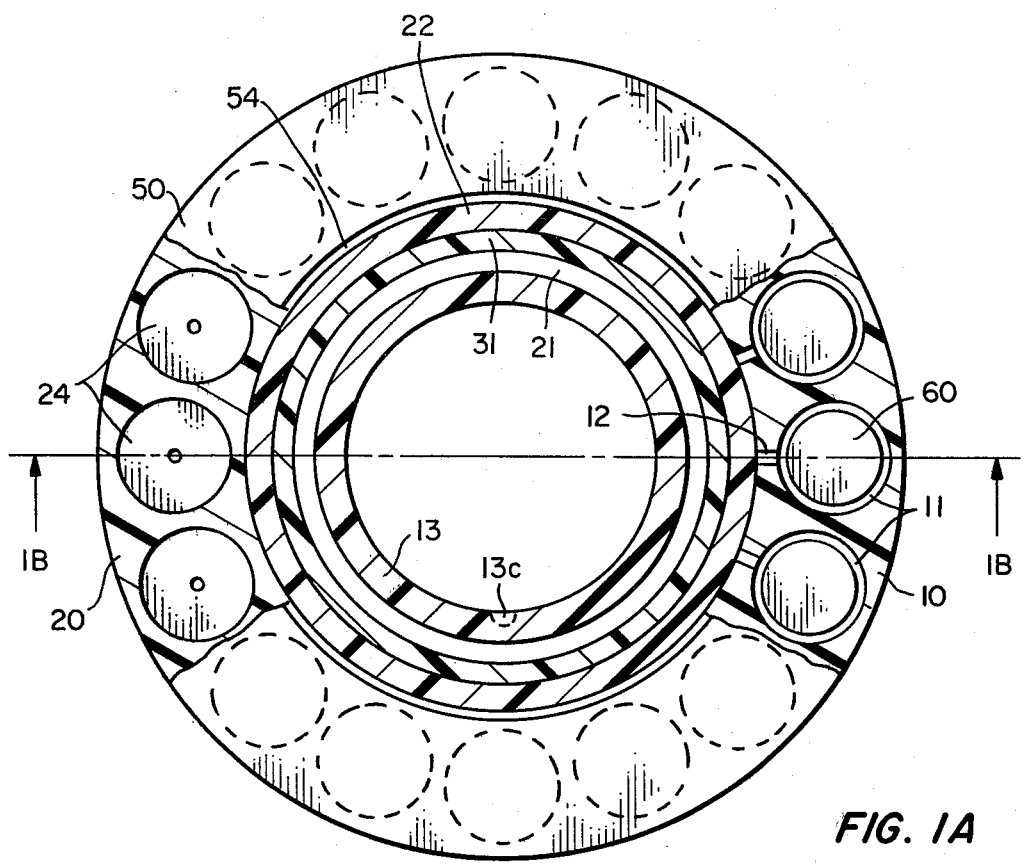
FIG. 1A is a top view of a first preferred embodiment of device for the identification of microorganisms or other diagnostic assays, according to the invention, taken through 1A—1A of FIG. 1B, in which a single screw type manipulation is required for operation.
Figure 1B:
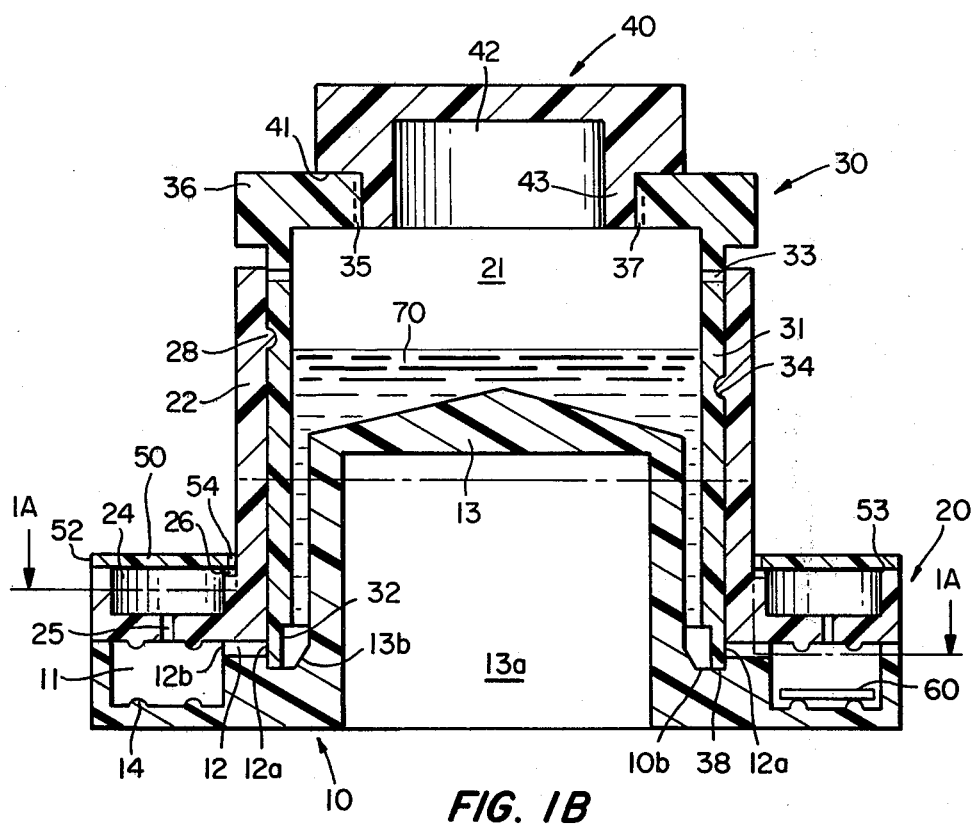
FIG. 1B is a cross-sectional side view taken through 1B—1B of FIG. 1A, and showing some detail not particularly illustrated in FIG. 1A.

In FIGS. 1A and 1B a first preferred embodiment of the invention is illustrated with a series (e.g. sixteen) of satellite testing chambers 11 arranged circumferentially and equispaced around a central chamber or reservoir 21. The number of satellite testing chambers 11 shown in the drawings is for illustration purposes only and is in no way intended to be limiting on the invention. The device may contain more or less satellite testing chambers depending, for example, on the particular types of diagnostic determinations for which it is intended.

It will also be appreciated that while the various embodiments specifically depicted herein are generally cylindrical in shape, a device according to the present invention may instead take a more or less rectangular form, with a trough-like centralized sample chamber running between two rows of analysis chambers, wherein an elongated member is associated with the sample chamber which has essentially the functions of the actuator element of the embodiment depicted in FIG. 4.

Figure 2:
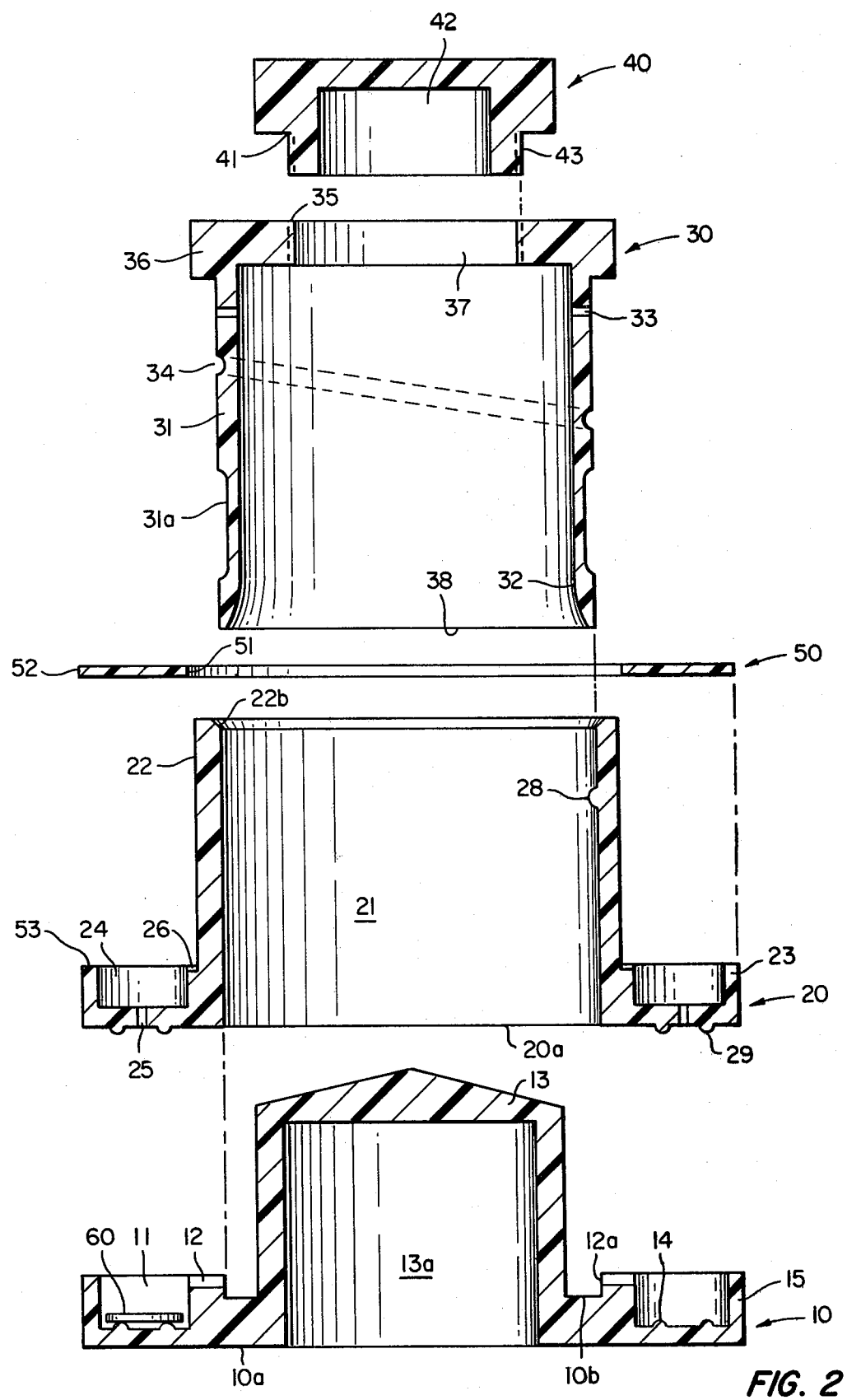
FIG. 2 is an exploded cross-sectional side view of the general device of FIGS. 1A and 1B, showing additional detail not particularly illustrated in FIGS. 1A and 1B.

While the preferred embodiments are illustrated as being comprised of five structurally mating pieces, i.e. a base or lower body portion 10, a cover or upper body portion 20, a sleeve type arrangement 30, a cap 40 and a disc-shaped seal 50, as is particularly shown in the exploded view of FIG. 2, it is to be appreciated that a lesser number of pieces may be employed to achieve the device according to the invention. For example, the device may be composed of essentially only two parts, i.e. the body and a movable sleeve or piston disposed within the central chamber 21, as can be more fully appreciated from later description. A suitable material for at least some (preferably all) of the pieces of the device, e.g. the lower body part, is clear styrene.

Each satellite testing chamber 11 contains one or more reagents, substrates, reactants or media (hereinafter variously also referred to as diagnostic substances) in solid disc-shaped form 60, as is more particularly described hereinafter. Elements 60 are variously referred to herein also as discs. The number of discs 60 illustrated in the drawings (e.g. FIG. 2 or 3) is not intended to be limiting on the invention. The satellite testing chambers 11 may contain two or more such discs, as is apparent e.g. from FIG. 7, depending on considerations, such as, for example, the type of assay being performed, compatibility of the reagents utilized in each chamber, and the like. Generally, the satellite testing chambers 11 will contain one or two such discs 60.

It is within the scope of the present invention to provide discs 60 as transparent support films bearing the diagnostic substances in solid, e.g. dried form.

Figure 3:
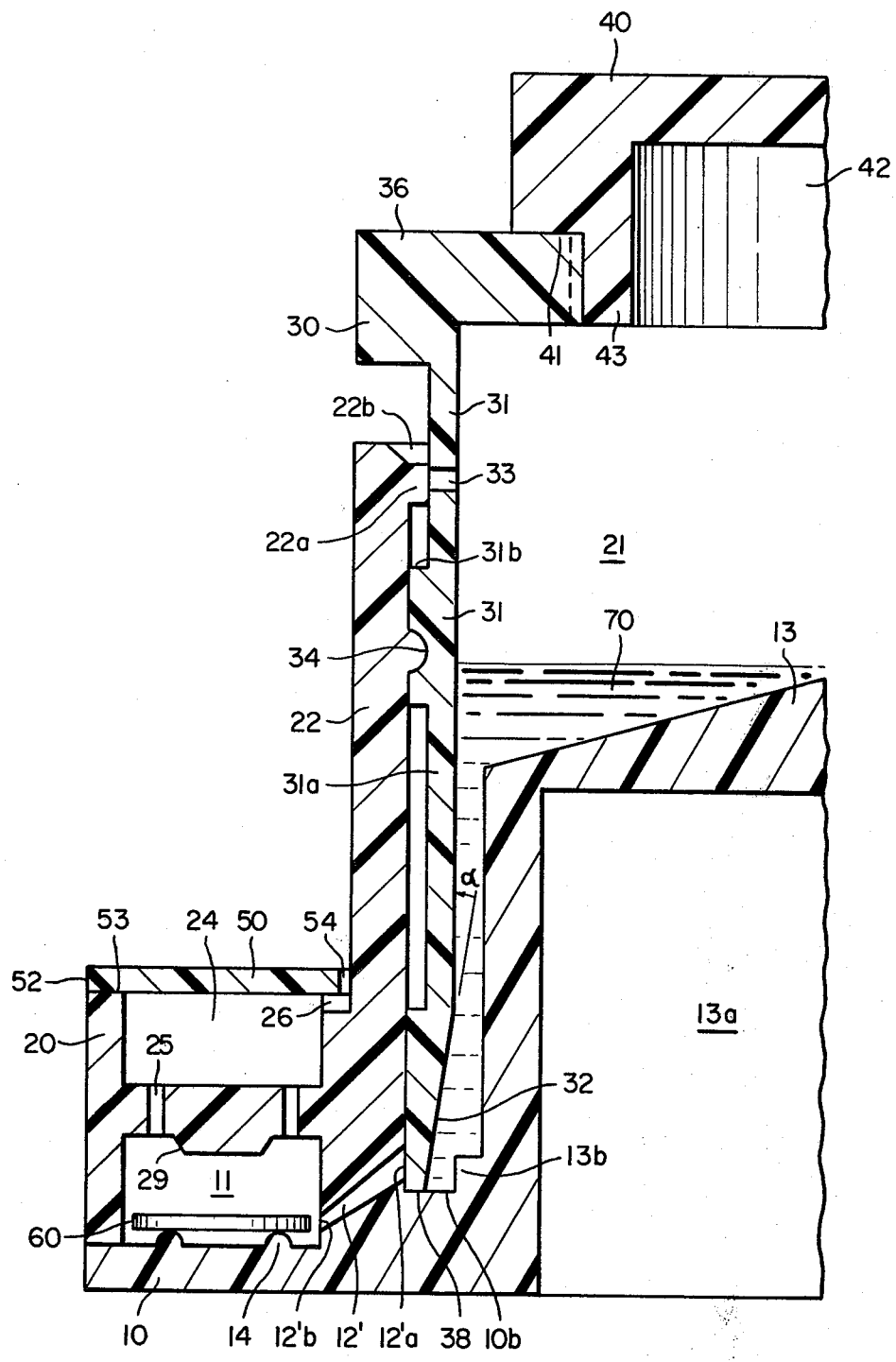
FIG. 3 is an enlarged cross-sectional side view of the left side portion of the device generally illustrated in FIGS. 1A-1B and 2, and showing further details not particularly illustrated in FIGS. 1A-1B and 2.

The satellite chambers 11 are preferably cylindrical in shape and are defined by the facing surfaces of the upper (20) and lower (10) body portions. Generally the lower body portion defines the bulk of the satellite chamber volume, with just the ceiling thereof being provided by the upper body portion 20 (see e.g. FIGS. 1-2). FIG. 3 illustrates, however, as example, that other satellite chamber definitions are possible between the cooperating upper and lower body parts. The dimensions of chambers 11 typically may run in the neighborhood of 0.25 inches in diameter and 0.2 inches deep. The array of satellite chambers, as aforesaid, can number sixteen, and thus be arranged every 22.5° of arc about the center of the device, forming a circle having a diameter in the neighborhood of 1.75 inches. Thus, the base or lower body portion 10 can typically have dimensions in the neighborhood of ¼ inch thickness from top to bottom and a 2.25 inch diameter.

Satellite chambers 11 are provided with small rounded bumps or protrusions 14 on the floor thereof. As particularly illustrated in FIG. 3, the bumps 14 raise the disc 60 off of the satellite chamber floor so as to facilitate access to the lower side of the disc by the sample fluid introduced into the chamber. An additional protrusion 29 is provided in the ceiling of each of the satellite chambers. Protrusion 29 is primarily intended to prevent disc 60 from floating up to close off venting passageways 25. Protrusion 29 can provide additional functions as will become apparent from the description hereinafter.

Although the cross-sectional views of FIGS. 1B, 2 and 3 show the floor protrusions 14 to be two in number, they are in actuality preferably three in number, equispaced apart. They can for example be triangularly arranged to define a circle having say a diameter in the neighborhood of 5/32 inches. Of course, protrusions 14 can be more than three in number or take alternative forms, such as a single slightly raised, flat-topped, substantially circular platform not unlike the shape of ceiling protrusion 29.

On the other hand, protrusion 29 can take other forms, such as a trio of rounded bumps, as illustrated for example in the view provided by FIG. 1B, substantially the same as the trio of raised protrusions 14.

Figure 7:
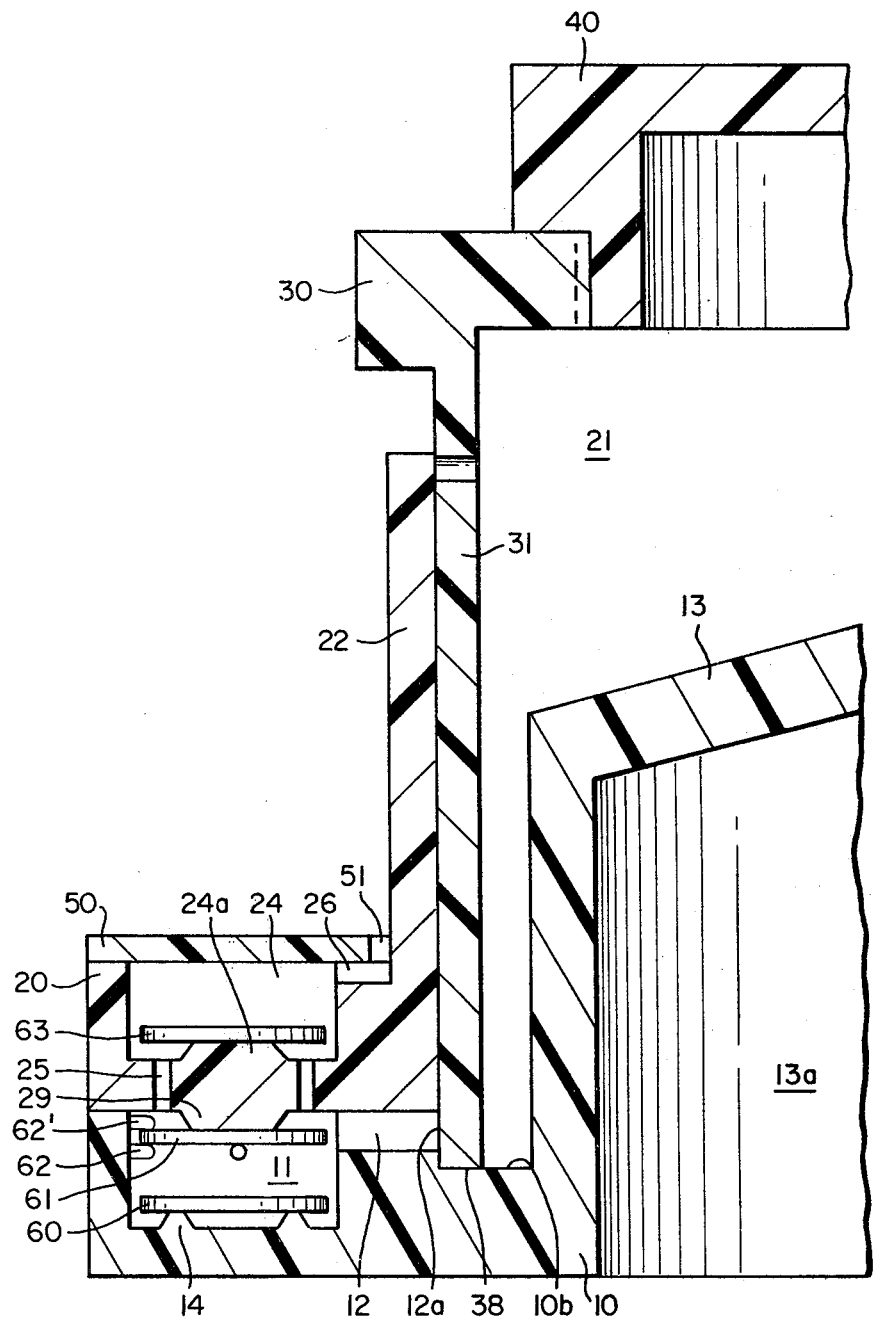
FIG. 7 is another enlarged cross-sectional side view of a device according to the invention, illustrating in particular various additional possible locations and configurations of the media discs.

The satellite testing chambers 11 are each connected to the central reservoir 21 by means of respective passages 12. FIGS. 1B and 7, as example, illustrate the passages 12 in a horizontal orientation, whereas a more preferred inclined orientation for passages 12 is shown in FIG. 3 (identified as passage 12'). The preferred passage 12' orientation of FIG. 3 particularly faciliates the loading or filling of the associated satellite chamber 11 with liquid sample from the central chamber 21. Passages 12/12' preferably have U-shaped cross-sections, having dimensions in the neighborhood of 0.08 inches in depth and width and 0.13 inches in length.

Each passage 12/12' communicates with the main or central chamber 21 via orifice 12a/12'a, preferably disposed (as shown e.g. in FIG. 3) slightly raised from the floor 10b of central chamber 21. Orifices 12a/12a' could, however, communicate with the central chamber 21 exactly at the floor 10b thereof.

For the point of communication of passages 12' with the satellite chambers 11 in FIG. 3, it is similarly preferred that the opening 12'b be disposed in the chamber wall a small distance from the chamber's floor. Passage 12 of FIGS. 1-2 and 4-5 on the other hand is shown disposed to communicate with the satellite testing chambers 11 at the top of the side wall thereof at 12b.

Inclined passage 12' is shown in FIG. 3 preferably with a slightly decreasing taper (from right to left). It will be appreciated, however, that passage 12 could have a uniform cross-section throughout its length or indeed having an increasing taper from right to left.

Regardless of which orientation or configuration of passages 12/12' is utilized, it is intended that all of such passages of the device adopt substantially the same dimensions and configuration.

The satellite testing chambers 11 are vented by one or more capillary passageways 25. For example, the views of FIGS. 1B and 2 show just a single passageway 25 centrally located relative to its satellite chamber 11, whereas the view of FIG. 3 shows two. A preferred arrangement comprises three passageways 25 disposed in the roof of each respective satellite chamber 11 equispaced apart in an arc of a circle having as its center the center of the microbe identification device itself. Alternatively, the three passageways 25 could be triangularly arranged equi-spaced apart in the roof of each of the satellite chambers 11. Typical dimensions for these passageways can be in the neighborhood of 0.02 inches in diameter and 0.06 inches in length.

The microbe identification device, or at least some of its parts, can be made of non-wetting type materials. Thus the vertical venting passageways 25, by virtue of their small size, coupled with the non-wetting property, can be made to effectively prevent accidental escape of liquid from the satellite chambers 11 to the remainder of the venting structure, and yet provide an unrestrained flow path for escaping air.

The venting passageways 25 lead to vent chambers or cavities 24. Preferably one such chamber is provided for each satellite chamber 11 and located directly above it. The venting chambers 24 in turn communicate with the atmosphere via respective horizontal and vertical capillary venting passageways 26 and 54. These venting passageways, as is the case with vent passages 25, faciliate the flow of liquid sample from the central chamber 21 into the satellite chambers by completing the air escape path, as well as offer protection against the escape of liquid from the chambers 11, while ensuring that the chambers are free from external contamination. The structural separation between the analysis chambers 11 and venting chambers 24 could instead be constructed of a porous non-wetting insert, i.e. a sintered material.

Passageways 26 typically can be U-shaped grooves in the top surface of the upper body portion 20, with dimensions in the neighborhood of 0.03 inches in depth and 0.06 inches in width, and are completed by placing seal disc 50 onto the top surface of upper body portion 20.

As is the case with passages 12/12', regardless of which orientation and/or configuration of venting passageways 26 and 54 is utilized, it is intended that the respective passageways adopt the same dimensions and configuration.

While the venting chambers 24 are shown in some of the figures (e.g. FIG. 3) as being of substantially the same size (volume) as the satellite chambers 11, it will be appreciated that the relative sizes of the two chambers can vary. It is preferred that chambers 24 be somewhat smaller than the satellite chambers 11 and have dimensions, for example, in the neighborhood of ⅛ inch deep with about the same diameter as the satellite chambers.

The two cooperating body portions 10 and 20 substantially fully define the central reservoir 21. The lower body part 10 preferably defines the floor 10b of the central reservoir and a major projection 13 from said floor, as well as the lowermost portion of the central chamber in the vicinity of orifices 12a. On the other hand the upper body part, in particular the vertical cylindrical part 22, provides the remainder of the central chamber wall.

Upper and lower body parts 20 and 10 may have coincident circumferences, as is illustrated in FIGS. 1B and 7. Alternatively upper body portion 20 may be provided with a lip 27 that overhangs a small portion of the lower body portion 10, as illustrated for example in FIG. 4B. Lip overhang 27 faciliates the assembly and sealing of the upper and lower body parts together. Lip 27 can be extended downwardly such that a large recess is in fact defined in the lower surface of body portion 20 in which the entirety of the lower body portion 10 can fit, as is illustrated for example in FIGS. 4C and 5A. The opposite case may also be provided, where the upper surface of lower body part 10 is provided with a major recess permitting the entirety of the upper body portion 20 to be snuggly placed therein.

The wall 22 of central chamber 21 is designed to snuggly receive a sleeve arrangement 30, which is constituted by a hollow, substantially cylindrically shaped body 31, fully opened at the lower end 38 and provided with a top portion which includes a flang 36 to facilate movement of the sleeve 30 and an aperture 37 having threads 35. Sleeve aperture 37 provides access to the central reservoir 21 when the sleeve 30 is assembled into the body 10/20 of the device, and thus allows sample 70 to be deposited into the central chamber 21. The sample can, of course, be pre-innoculated or can be innoculated in the central chamber itself.

Sleeve arrangement 30 is provided with a cap 40 for covering aperture 37. The cap shown in FIGS. 1-5 is substantially hollow (at 42) and has a threaded lower portion 43 of lesser diameter sized to closely cooperate with the threaded opening 37 of the sleeve 30. The wider-diameter top portion facilates the sealing of the central chamber at 41.

Alternatively, cap 40 could be replaced, for example, by a relatively thin layer of suitable material, such as the material from which the sleeve arrangement 30 is made, covering the opening 37 of the sleeve 30, which thin layer would be readily penetrable, for example, by a needle syringe device.

In the embodiments disclosed in FIGS. 1-5, a venting arrangement is provided for central chamber 21, which is fully defined by the sleeve 30 in conjunction with the vertical wall portion 22. Venting apertures 33 are provided in the sleeve wall 31 which cooperate with venting means provided in the cylindrical wall 22. For example, in FIG. 2 the venting means is provided by a suitable bevel 22b on the inside top surface of the main chamber wall 22, as will be more fully explained hereinafter in connection with the first preferred embodiment which has a screw type or inclined cam actuation. This type of arrangement may also be used in connection with the second preferred embodiment (as shown in FIG. 4B) which employs a linear vertical displacement type movement of the sleeve to effect a filling of the satellite chambers.

Figure 4A:
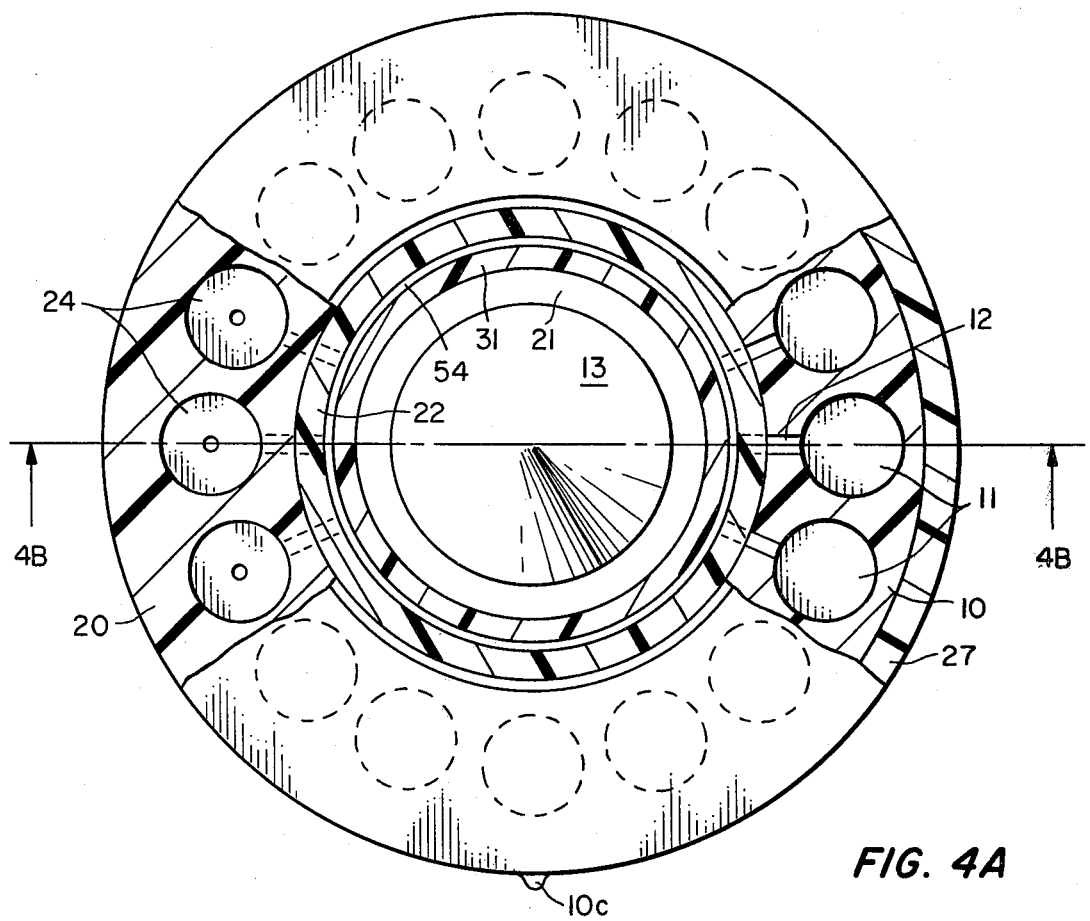
FIGS. 4A and 4B are respectively top and cross-sectional side views of a second preferred embodiment according to the invention, in which a vertical linear manipulation is required for operation, with the view of FIG. 4A taken through 4A—4A of FIG. 4B and the view of FIG. 4B taken through 4B—4B of FIG. 4A.
Figure 4B:
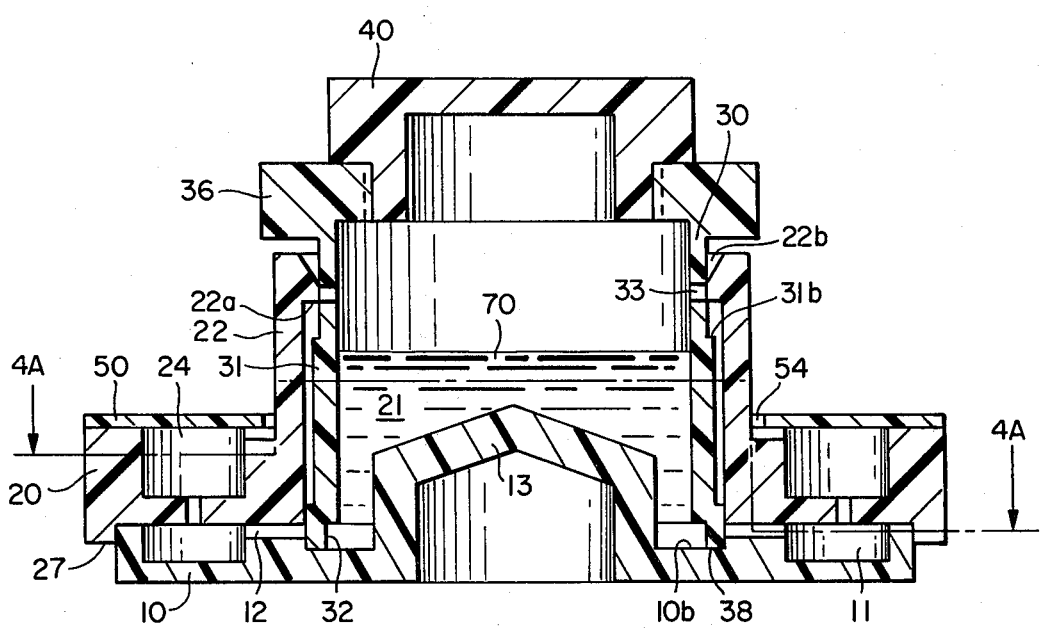
Figure 4C:
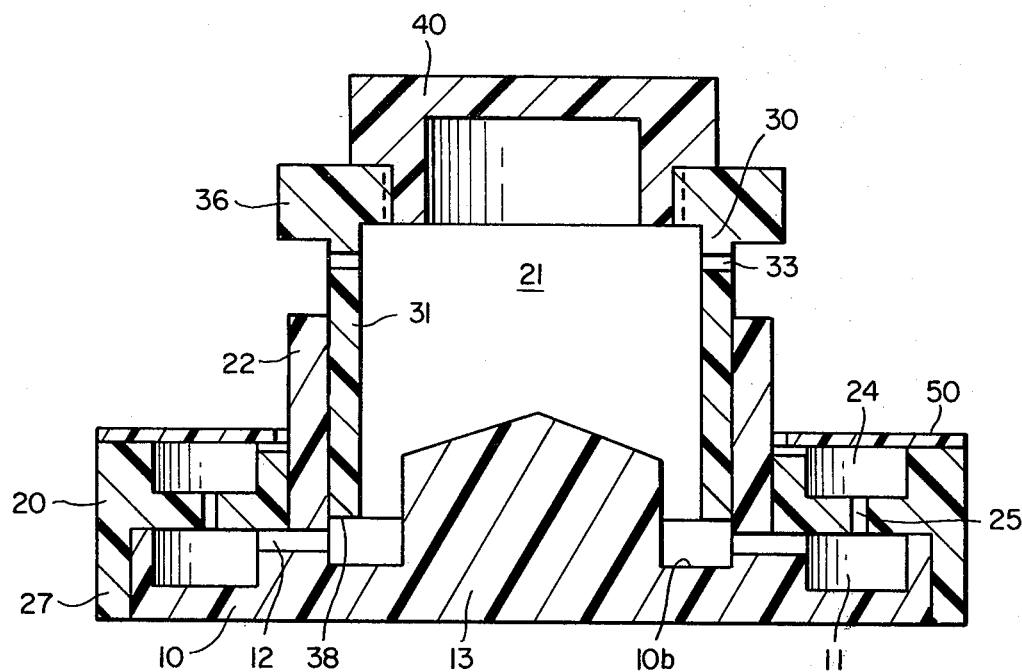
FIG. 4C is a simplified cross-sectional side view illustrating a subembodiment of the general device of FIGS. 4A and 4B in the actuated mode.

Alternatively, the venting means could comprise the chamber wall simply having an appropriate height, as shown in FIGS. 1B and 4C. Also, the central chamber wall 22, whether defined by upper body portion 20 as e.g. in FIGS. 1-3 and 4B, or by lower body portion 10, as e.g. in FIG. 4C, could be provided with cooperating venting apertures. The venting apertures 122c are illustrated for example in the arrangement shown in FIG. 5A. FIG. 5A depicts the third preferred embodiment, which employs a simple, short purely rotary movement of the sleeve to actuate the device. The venting apertures 122c, like the sleeve apertures 33, may be dimensioned in the neighborhood of 5/64th inches in diameter and can typically be anywhere from one to four or more in number, suitably disposed about the circumference of sleeve wall 31 and chamber wall 22 respectively. Such an arrangement insures that the central chamber wall 22 is made sufficiently high without difficulty.

As can be gathered from FIGS. 1-5, several designs of the sleeve/plunger or piston 30 are disclosed. These vary structurally primarily on the basis of the precise simple movement employed to actuate the device, as will be more fully appreciated hereinafter.

The embodiments depicted in FIGS. 1-5 and 7 show disposed in central chamber 21 member 13, preferably substantially cylindrical in shape, projecting upward from the base portion 10. Projecting member 13 occupies a relatively large portion of the total possible volume of central chamber 21 as defined by the upper and lower body portions 10, 20 and sleeve 30. Projecting member 13 is preferably domed or peaked as shown e.g. in FIG. 3. The portion 13a of lower body portion 10 which comprises the projecting part can either be hollow, as e.g. in FIGS. 1-3, or solid, as e.g. in FIGS. 4 and 5. Domed projection 13 has as its primary function to increase the hydrostatic head of the relatively small quantity of sample 70 provided in the central chamber 21. This facilates the uniform simultaneous filling of the satellite chambers and forces the sample introduced into the chamber 21 to be initially gathered in the vicinity of the lower periphery of chamber 21 where the openings 12a/12a' to the passages 12/12' leading to the satellite chambers 11 are located.

Projection 13 can be provided with one or more indexing tabs or recess 13c, as shown in FIG. 1A, on the inner vertical surface of area 13a. Tab or recess 13c provides a means of operator or machine identification of satellite chamber location. Alternatively such tab or recess means could be provided as shown in FIG. 4A as element 10c, located on the periphery of the base portion 10.

The height of the domed projection can be varied according to particular application, such as to receive more or less sample in the main chamber 21, or to accommodate more viscous substances. Typical dimensions for the projection 13, as embodied for example in FIG. 1B can be in the neighborhood of one inch in diameter, with a height relative to the floor 10b of the main chamber 21 of ¾ of an inch. Normally, a relatively high projection 13 is preferred since all too often the amount of available sample is quite small.

Domed projection 13 may be provided with an annular slope (FIG. 1B) or ledge (FIG. 3) 13b proximate the floor 10b of the central chamber 21. Its chief purpose is to further facilitate the gathering of the sample fluid 70 at the lower periphery of the central chamber and thereby the flow of the sample into the satellite chambers 11.

The cylindrically shaped central chamber 21, as defined by the vertical wall 22 of either the upper body part 20 (e.g. FIG. 3) or by the lower body part 10 (e.g. FIG. 4C), can typically have dimensions in the neighborhood of 1.2 inches in diameter, and as defined by the sleeve arrangement 30 a height from the bottom surface 38 to the venting port(s) 33 typically in the neighborhood of one inch and a diameter of substantially the same.

The device of most embodiments described herein is completed with a seal disc 50 received onto the top surface 53 of upper body part 20 (e.g. FIG. 3). The seal disc 50 is provided with a central aperture 51 (FIG. 2) having a diameter slightly larger than the outer diameter of chamber wall 22, thus defining the annular relief slot 54 which completes the venting path from the satellite chambers 11 that includes venting passageways 25 and 26 as well as venting chamber 24.

Seal disc 50 generally has a circumference whereby the outer surface 52 is substantially flush with the side wall of the upper body portion 20, as shown in the figures. However, it may have a lip overhanging the uppermost outer portion of upper body portion 20, to facilitate the seal between the seal disc 50 and body portion 20. Seal disc 50 may be applied to the surface 53 by any suitable means including adhesive. Seal disc 50, like the upper and lower body parts 20 and 10, is preferably made of optically transparent material.

With particular regard to the first preferred embodiment, as illustrated in FIGS. 1-3, actuation of the device, i.e. allowing or causing the sample fluid 70 deposited in the central chamber 21 to flow uniformly and simultaneously into the satellite testing chambers 11, is effected, as indicated above, via a simple screw type or cam movement of the sleeve 30. The sample can be deposited in the central chamber 21 of the assembled device by, for example, a pipette (not particularly shown) and innoculated, through the aperture 37 in the sleeve arrangement 30. The cap 40 (if such is used) is then screwed onto the sleeve 30 and the device shaken vigorously, making sure beforehand that the sleeve 30 is in its lowermost position, thus sealing off the apertures 12a (see e.g. FIG. 3).

The microbe identification device is then laid upright on a surface and the innoculated sample allowed to gather uniformly in the lowermost portion of the central chamber 21. To this end, the lower part of the sleeve wall 31 is provided with a beveled inner surface 32 at its bottom 38 (e.g. FIG. 3) which further allows the sample to be gathered proximate the openings 12a to facilitate the uniform, simultaneous, rapid flow of sample into the satellite chambers 11.

As shown in FIG. 3, beveled inner surface 32 forms an angle α with respect to the vertical, which can be for example in the neighborhood of 10°. Alternatively, bevel 32 can instead be an annular recess 32, such as is shown in FIG. 1B.

To actuate the device of FIGS. 1-3, flange 36 of the sleeve is gripped by the fingers and turned a small amount. This turning causes the sleeve to be raised such that the bottom portion 38 thereof clears the openings 12a/12'a of the passages 12/12'. This type of movement is effected by a single thread or inclined groove arrangement 34 provided on the outer surface of wall 31 of the sleeve 30 and a protrusion 28 of cooperating shape projecting inwardly from the inner surface of the central chamber wall 22. See particularly FIG. 2. Cam channel or groove 34 can typically have a 270° inclined wrap around sleeve 30, with say a pitch of 5/32 inches.

To prevent accidental excessive retraction or withdrawal of the sleeve arrangement 30, central chamber wall 22 and sleeve wall 31 can be provided with respective parts of a detent stop arrangement 22a and 31b (FIG. 3). The configuration and location of detent stop parts 22a and 31b are such as to enable central chamber vent port 33 to communicate with the atmosphere with the sleeve 30 in the fully retracted position, via bevel 22b in central chamber wall 22. Of course, the ends of the cam groove or inclined slot 34 can provide in their own right a form of limit stop arrangement.

The sleeve wall 31 is made somewhat resilient (e.g. polyethylene or polypropylene) to facilitate its assembly into the central chamber area. To this end, the sleeve wall 31 may be narrowed at 31a between beveled end 31 and the cam groove area 34 (FIGS. 2 or 3). This narrowing creates a gap between the sleeve wall 31 and the central chamber wall 22 which also advantageously reduces the contact friction between these two surfaces.

Figure 5C:
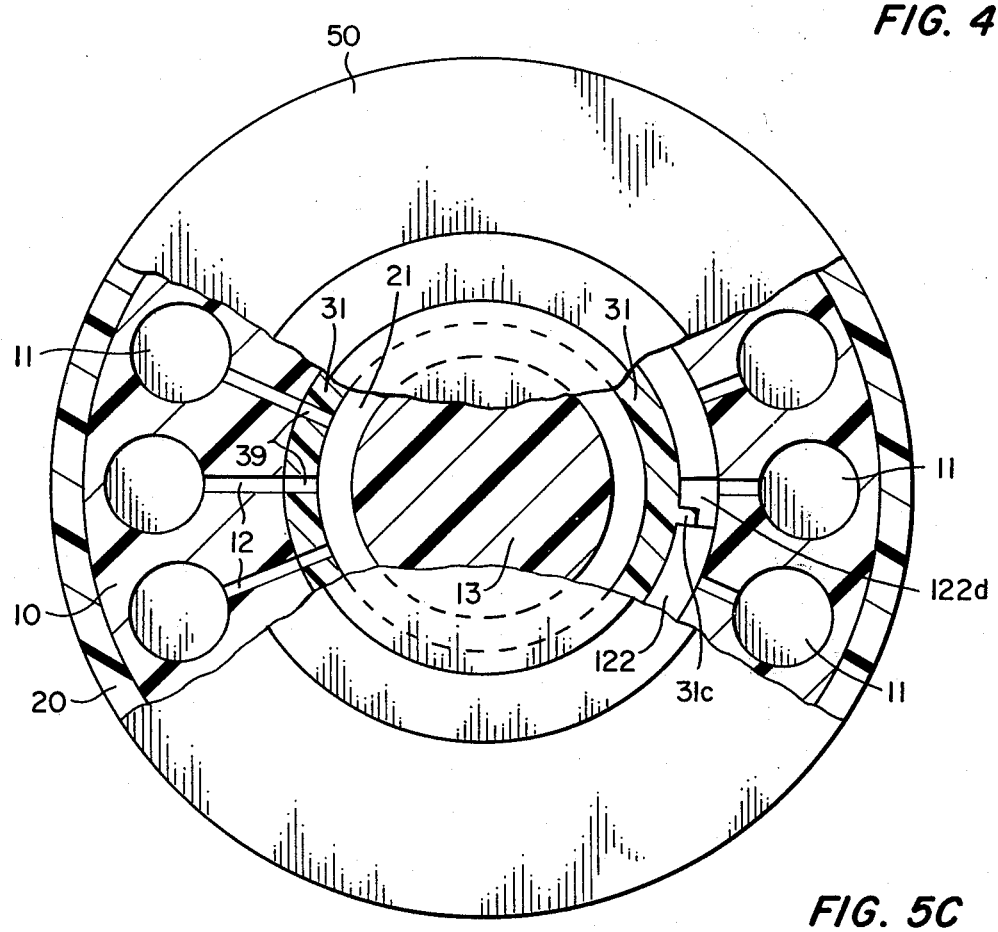
FIG. 5C is a top view illustrating the device of FIGS. 5A and 5B in the actuated mode.
Figure 5B:
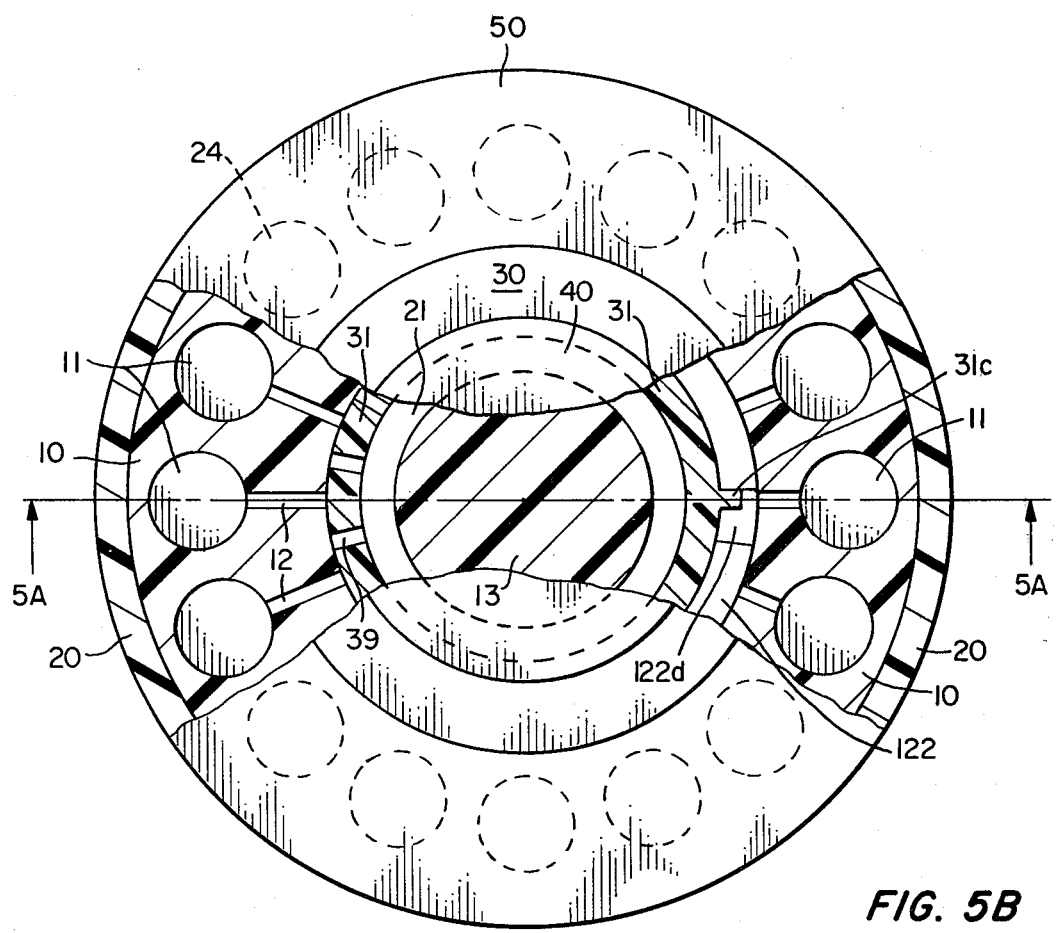
FIGS. 5A and 5B are respectively top and cross-sectional side views of a third preferred embodiment according to the invention in which a short, purely rotational movement is required for actuation, with the view of FIG. 5A taken through 5A—5A of FIG. 5B and the view of FIG. 5B taken through 5B—5B of FIG. 5A.
Figure 5A:
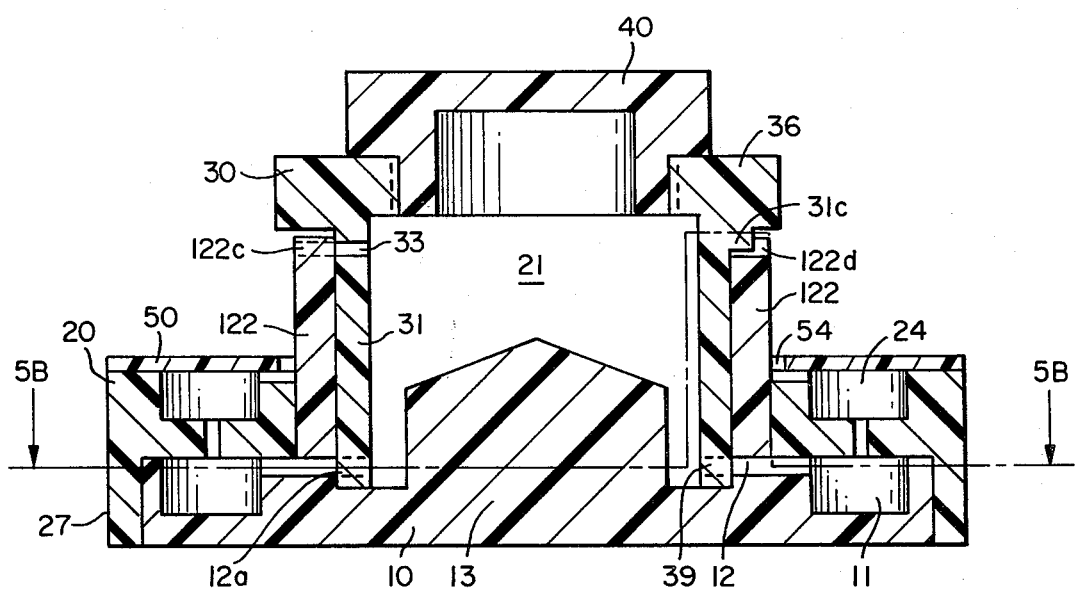

The sleeve actuator arrangement 30 depicted in FIGS. 1-3 thus defines a single thread or groove cam assembly which can be considered a hybrid arrangement between the fully linear vertical movement required of the arrangement illustrated in FIGS. 4A-4C and the purely rotary movement required in the arrangement illustrated in FIGS. 5A-5C.

The screw type or cam movement of FIGS. 1-3 also aids the hydrostatic head and yet minimizes a tendency of the sample to be introduced into the venting arrangement associated to each of the satellite chambers, when the device is actuated. This can be particularly appreciated when considering that the movement of the sleeve relative to the openings 12a/12'a of the passages 12/12' is an upward/sideward sliding motion past these openings which minimizes any possible displacement shock which might be caused by a more abrupt movement.

It will, of course, be appreciated that two or more cam type arrangements can be provided in the respective walls of the sleeve 30 and upper body part 22. Moreover, walls 31 and 22 could instead be provided with cooperating threading, providing as example a single thread coupling.

Once the sleeve has been manipulated as described above, from the starting position wherein the bottom of the sleeve 38 is in contact with the floor 10b of chamber 21, the sample 70 flows through the now-opened passageways 12/12' simultaneously and rapidly into the satellite chambers 11, thus automatically filling the latter with sample. The sample interacts with the solid material disc 60 to provide test results, as is more fully described hereinafter. The air displaced by the sample is vented through to the atmosphere as hereinbefore described via passages 25, 26 and 54 and venting chambers 24.

In the second preferred embodiment, which is depicted in FIGS. 4A-4C, only a single, reversible linear vertical movement of the sleeve arrangement 30 is needed to activate the device. In either of the sub-embodiments depicted in FIGS. 4B and 4C, such a movement not only allows sample to enter the satellite chamber, it raises the sleeve venting ports 33 to fully communicate wwith the atmosphere. The sleeve wall 31 can contain anywhere from one to four (or more) equi-spaced venting ports 33 which vent the central reservoir 21 when the sleeve 30 is in the raised position as illustrated in FIG. 4C. As in FIG. 3, sleeve arrangement 30 of the second preferred embodiment can be provided with a detent stop arrangement 22a/31b and a recessed lower end 32 of sleeve wall 31.

As before, the movable sleeve 30 is initially in the closed position with the cap removed for receiving fluid sample. In this position, the bottom surface 38 of sleeve 30 contacts the base 10b of the central reservoir 21 thus preventing any of the fluid sample 70 from prematurely entering passages 12 leading to the satellite testing chambers 11.

After the sample is loaded into central chamber 21 and the cap 40 replaced and the sample allowed to settle after shaking, movable sleeve 30 is raised via gripping flang 36 to the extent necessary to expose venting apertures 33, thereby venting central reservoir 21 and allowing the fluid sample 70 to flow into satellite testing chambers 11 via passages 12. This activated position is demonstrated in FIG. 4C.

Any convenient means of indicating to the user the extent to which movable sleeve 30 should be raised can be utilized, such as the detent stop arrangement particularly illustrated in FIG. 4B.

It can be gathered from a comparison of the sub-embodiments of FIGS. 3 and 4B that the definition of the satellite testing chambers 11 is indeed shared by the upper and lower body portions 20 and 10. In the case of FIG. 4B, as example, the top of the chambers 11 is defined by the lower surface of the upper body part 20. In FIG. 3, on the other hand, upper body portion 20 defines substantially all but the bottom surface of chambers 11. It can be appreciated that various arrangements intermediate between these two cases are fully possible.

In this way, also, passages 12 can be formed at the junction of body portions 10 and 20. The openings of horizontal passageways 12 into chambers 11 can in fact be located anywhere in the chamber wall depending for example on how the volume of the chambers 11 is to be shared between the upper and lower body portions 20 and 10 and where the chambers are located in height relative to the central chamber. It will also be appreciated from the depicted sharing arrangement in FIG. 3, that the inclined passageway 12' can be created whereby the top half could be provided by a suitable groove in the bottom surface of the upper body part 20 and the lower half provided by a suitable cooperating groove in the upper surface of lower body part 10.

Reference is made to FIGS. 5A–5C which illustrate the third preferred embodiment of the invention. In this embodiment, a rotatable sleeve 30, located as before in central reservoir 21, is provided at its lower end with a number of apertures 39, equaling the number of passages 12 leading to satellite testing chambers 11. The apertures 39 are equispaced in sleeve 30 so that, upon rotation of the sleeve from a "closed" position, as illustrated in FIG. 5B, to the "activate" position, as illustrated in FIG. 5C, they will align with the openings 12a of passages 12, thus permitting the flow of fluid sample 70 from central reservoir 21 into satellite testing chambers 11. All of the apertures 39 should have the same dimensions.

In FIGS. 5A and 5B, the rotable sleeve 30 is shown in the closed position. Fluid sample 70 (not particularly illustrated) has been placed in central reservoir 21 through the sleeve orifice and the cap 40 replaced. Rotatable sleeve 30 in this position is blocking the openings 12a to passages 12 (FIG. 5B); thus no fluid may leave the central reservoir 21. This is true also with regard to venting ports 33/122c.

In the sub-embodiment of FIG. 5B, the lower body portion 10 defines the central reservoir 21 and is provided with the plurality of vent apertures 122c. The venting apertures 122c are intended to align with apertures 33 in rotatable sleeve 30 for venting the central reservoir 21 only when the latter is rotated into position for filling the satellite chambers 11.

Movement of the sleeve 30 is facilitated as before by gripping flang 36. Of course, the sleeve may be arranged to rotate in either clockwise or counter-clockwise direction to effect alignment of the sample flow and venting apertures. And, suitable means, such as detent stops (illustrated in FIG. 5B as elements 31c and 122d) may be utilized at the interface of the sleeve wall 31 and the wall of the central chamber to limit the rotation of sleeve 30 so that proper alignment is assured, and in one direction of rotation only, if desired.

As is the case with the other preferred embodiments, after the satellite chambers 11 have been filled, sleeve 30 is returned to its original closed position, thus sealing both the openings of passages 12 and the venting apertures 122c. Venting of the air in satellite chambers 11 takes place as in the manner described for example with reference to FIG. 3.

Figure 6A:
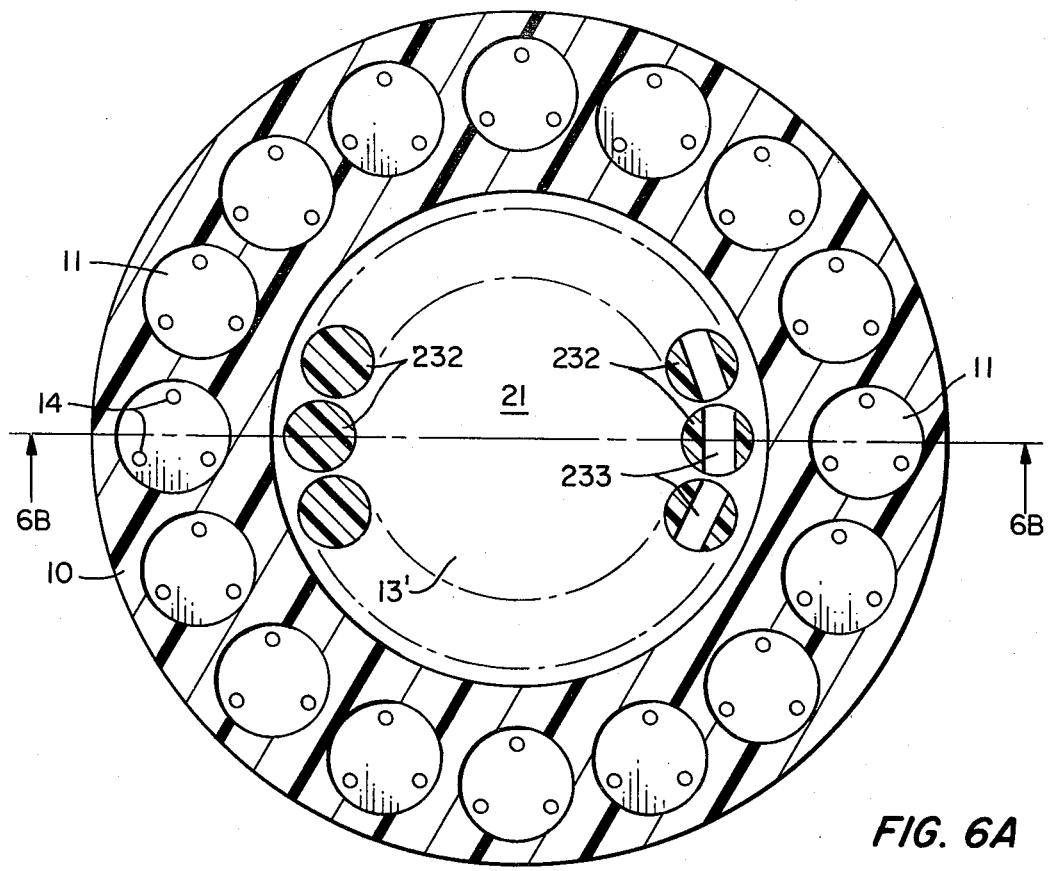
FIGS. 6A and 6B are top and cross-sectional side views respectively of a further embodiment of the invention, which employs a screw-piston arrangement for operation.
Figure 6B:
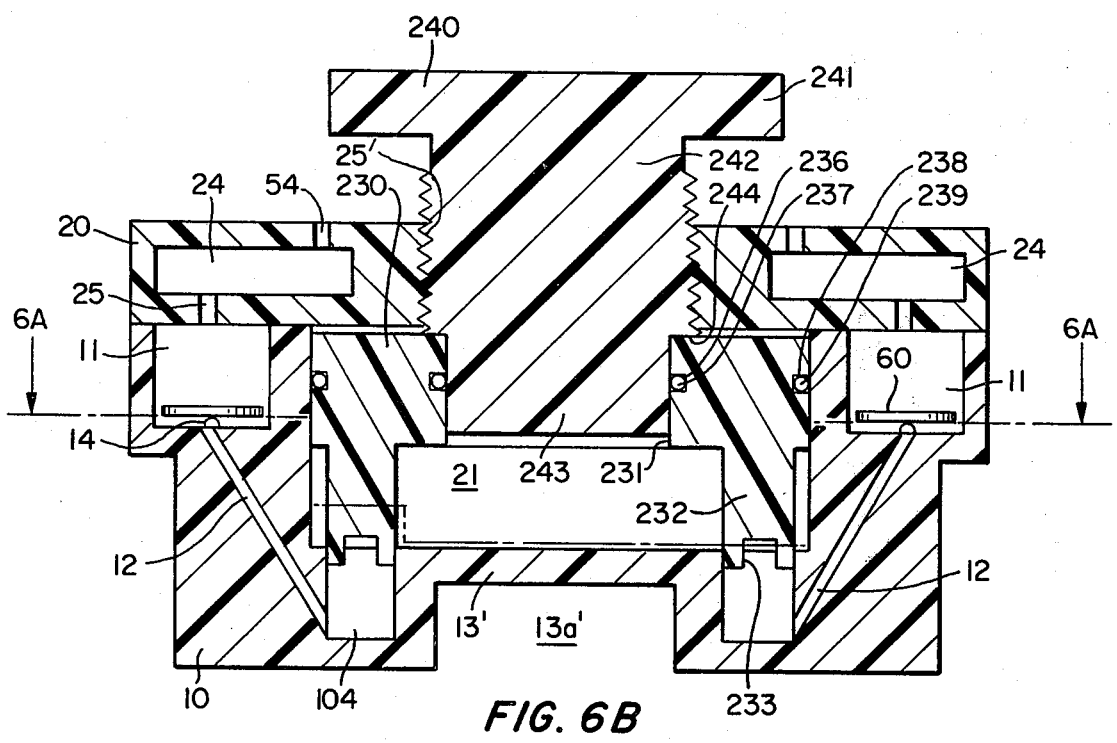

FIGS. 6A and 6B illustrate in respective top and cross-sectional side views a further embodiment of the invention, which employs a piston type actuation effected by a screw type movement. The embodiment of FIGS. 6A and 6B is an example of the device according to the invention being constructed from a reduced number of main parts, i.e. a base or lower body portion 10, a cover or upper body portion 20 and the screw/piston actuator 230/240. In the embodiment of FIGS. 6A and 6B, both the central reservoir 21 and the satellite chambers 11 are virtually fully defined by the lower body portion 10. As before, the satellite chambers 11 have a communication path to the central chamber 21 which includes capillary passages 12. Moreover, satellite testing chambers 11 are vented via a venting arrangement which includes verticle capillary passage 25, venting chamber 24 and capillary passage 54 which leads to the atmosphere.

In this embodiment there is combined a special piston arrangement 230 and screw cap actuator 240. Piston 230 is provided with a multiplicity of satellite pistons 232 projecting from the lower surface thereof, one for each of the satellite chambers 11. The satellite pistons 232 are intended to be received in cooperatively disposed recesses or cylinders 104 in floor of the main chamber 21. Thus, passages 12 connect the satellite chambers 11 with the main chamber 21 via the satellite cylinders 104.

In the embodiment depicted in FIG. 6B the satellite chambers 11 are significantly elevated with regard to the satellite cylinders 104, and therefore passageways 12 are rather steeply inclined from the latter to the former, communicating at each end with the floor area of chambers 11 and satellite cylinders 104.

The main floor of central chamber 21 is provided by section 13', somewhat similarly to previously discussed embodiments, including the inclusion of a hollowed area 13a'. The placement of floor section 13' as shown, together with the sidewalls defining main chamber 21, locates the satellite cylinders 104 somewhat away from the side wall of main chamber 21. As such, the satellite pistons are correspondingly positioned inward somewhat from the side edge of the main piston 230.

Main piston 230 is provided with an outer recess 238 which houses an O-ring 239 intended to prevent sample leakage around the periphery of the main piston. Main piston 230 is provided further with a central bore 231 for housing the lower portion 243 of screw cap 240. In the wall of bore 231 is an annular recess 236 for housing a second O-ring 237 which is provided for the same reasons as O-ring 239.

Screw cap 240 is provided with an upper flang portion 241 to facilitate its rotation, and a middle threaded portion 242 which is designed to be received in a central threaded bore 251 in upper body portion 20. Threaded cap 240 is also provided with an annular horizontal surface 244 constructed to engage with the top surface of main piston 230, designed to urge main piston 230 downward when screw cap 240 is threaded into the central bore 251 of the upper body portion 20.

Satellite pistons 232 are provided with rectangular recesses 233 in the lower surfaces thereof which are designed to provide access to the satellite cylinders 104 for the sample which is introduced into main chamber 21, when main piston 230 is in its retracted position as shown in FIG. 6B.

In operation, when the device illustrated in FIGS. 6A and 6B is assembled, main piston 230 may be placed in its retracted position as shown, with the friction provided by O-ring 239 allowing main piston 232 to be maintained in this position in the absence of a positive force being exerted thereon by screw cap 240. Screw cap 240 is withdrawn thus creating a access path to main chamber 21 through the threaded bore 251 of upper body part 20 and central bore 231 of main piston 230, thereby allowing sample to be introduced into the main chamber for distribution to the satellite chambers 11. The screw cap 240 is then replaced and the position shown in FIG. 6B again assumed. Then, as cap 240 is screwed further downward into position, ledge 244 engages with the upper surface of main piston 230 thus urging the latter in a downward motion.

In the meantime, the sample which has been introduced into the main chamber 21 has been allowed to flow into and fill satellite cylinders 104 via the access recesses 233 in the satellite pistons 232. A continued screwing motion of cap 240 eventually brings the downward movement of main piston 230 to the boint where the recesses 233 in satellite pistons 232 pass below the floor of the main chamber 21, thus sealing off the sample in cylinders 104 in measured amount. The continued turning of cap 240 results in a gradual further downward movement of main piston 230, which forces the sample up through the inclined passageways 12 into the respective satellite chambers 11, there to interact with the respective discs 60, as before.

The screw type piston actuation provided by the device of FIGS. 6A and 6B offers two immediate advantages. By the fine cooperative threading providing between cap 240 and the threaded central bore 251 of upper body part 20, the introduction of sample into the satellite chambers 11 is gradual and orderly and thus eliminates the possibility of a "weeping" of the sample into the venting arrangements provided for the satellite chambers. Secondly, once the main piston 230 has been urged downwardly to fully dispense sample contained in the satellite cylinders 104 to the satellite chambers 11, the main piston is retained in that position, thus preventing any back flow of the sample. The elimination of back flow is facilitated by the blocking of the passages 12 at the lower end by the satellite pistons 233 in their lowermost assumed position. Additionally the arrangement of FIGS. 6A and 6B could be provided with a simple lock mechanism which is engaged with the final turn of cap 240, thus ensuring that the full activate position is maintained.

In FIG. 7, a second enlarged cross-sectional view of a portion of preferred embodiment of device according to the invention is illustrated, which particularly illustrates a single satellite testing chamber 11 and its corresponding venting arrangement. As is the case with earlier-described embodiments, the satellite testing chamber 11 is provided with projections 14 and 29 from the floor and ceiling surfaces thereof respectively. The projections 14 on the lower surface can serve as bases upon which to rest or secure the disc 60 and to elevate the disc so that sample may flow under and around it thus enabling full contact with the upper and lower surfaces thereof. In this way, the sample can simultaneously contact two different and potentially incompatable reagents coated on the respective disc surfaces, as will be more fully appreciated hereinafter.

The device according to the invention is designed such that each of the satellite chambers 11 receives a uniform amount of sample. In the case of the embodiments depicted in FIGS. 1–5 and 7, the amount of sample is defined by the capacity of the satellite chambers per se, whereas in the embodiment of FIG. 6, the uniform amount is defined by the satellite cylinders 104 and pistons 232/233. It will be appreciated that the amount of sample introduced into the central reservoir should be somewhat in excess of the amount required to substantially fill all of the satellite testing chambers.

In FIG. 7, as alluded to hereinbefore, projection 29 from the ceiling of the satellite chamber can serve additional purposes. As shown, it may be utilized as a carrier for a second disc material 61 which enables the second disc to remain fully apart and out of contact with the initial disc 60.

With particular regard to the embodiment depicted in FIGS. 6A and 6B, the second disc material 61 can readily remain initially above the level of sample allowed to enter the satellite chamber 11. In this way particularly a secondary reaction may be initiated at a later time simply by turning the device upside down. Of course, also, secondary disc 61 enables the inclusion in satellite chamber 11 of additional potentially imcompatable reagent or substrate substances. With the introduction of the secondary disc 61, it is now possible to provide at least four potentially incompatable substances, one on each of the separate broad surfaces of the primary and secondary discs 60 and 61.

Secondary disc 61 can be suspended from projection 29 by any suitable means that will not influence the reaction(s) intended to take place in chamber 11, such as by suitable adhesive. Alternatively, secondary disc 61 can be supported near the top of chamber 11 via an inert porous web or other means which would be attached to the upper side walls of the satellite chambers. In this latter regard, FIG. 7 illustrates small projections 62 from the side wall of the satellite chamber. The projections 62 may be several in number and variously located around the cylindrical wall of the satellite chamber, as shown, or alternatively could be an annular projecting ring. Secondary disc 61 could be placed on projections 62 just prior to assembly of the top body portion 20 to the main or lower body portion 10.

A further variation of means for suspending secondary disc 61 would be to provide a second annular ring or second series of projections 62' above the initial projections 62, thus enabling the disc to be snapped or otherwise held in place between the upper and lower projections.

FIG. 7 also illustrates the possibility of providing yet a third disc 63, located, however, in the venting chamber 24. As shown, third disc 63 may be supported above the floor of the venting chamber 24 via a projection 24a having similar function to that of projections 14 located in the floor of satellite chamber 11. Third disc 63 may be placed into the venting chamber 24 just prior to the seal disc 50 being assembled to the upper surface of the body portion 20. Third disc 63 may, like discs 61 and 62, contain substances useful in identification, coated in dry form onto either or both broad surfaces thereof.

Use may be made of third disc 63 particularly where a secondary or tertiary reaction is desired and one or more by-products of the earlier reaction(s) generate a volatile substance which is able to easily pass through capillary passages 25, as will be more fully appreciated from examples described hereinafter.

In a typical general application of the device, after the sample has been allowed to enter the satellite testing chambers, the device can then be incubated for an appropriate time to allow, for example, for bacterial growth and/or a color reaction to take place. The period of incubation would, of course, be dependent on the time required for the diagnostic determination(s) being conducted.

It is entirely within the scope of this invention to initially place an appropriate culture medium in the central reservoir 21 and then innoculate that medium with the sample to be tested. In this instance, it is contemplated that the device would be incubated for an appropriate time to allow bacterial growth to take place before the innoculated medium is introduced into the satellite testing chambers.

The device of the present invention can conveniently be manufactured from any suitable, preferably substantially rigid, plastic material, such as is discussed hereinafter, especially with regard to the discs 60. It will be appreciated that, at least a portion of the device which defines the satellite testing chambers should be constructed of optically transparent material to permit the best visual and/or machine inspection of the results of the various activities and reactions carried out in the satellite chambers, without disassembling the device. The device may be read and interpreted manually or through the use of automated equipment recognized in the diagnostic arts as being suitable for such purposes. Once this has been carried out, the device may be discarded. Alternatively, assembly of the device could be such as to permit the device to be reused in subsequent determinations. In such an instance the device would be disassembled, cleaned, sterilized and then fresh diagnostic substances (reagent or substrate discs 60) inserted into the satellite testing chambers 11.

The discs or media support films 60 contained in the satellite testing chambers are comprised of a base support material in film thickness, one or more diagnostic substances, i.e. substrates, reagents or media, and a film-forming substance for enabling the diagnostic substances to be coated onto the support. The support is comprised of suitable, non-water soluble, impermeable, substantially transparent material, preferably a plastics material having some flexibility which, is compatible with the microbes to be identified, the diagnostic substances to be used in the identification, and the substances used for enabling the substrates or reagents to be coated onto the support, such as, for example, polystyrene, polystyrene copolymers, polypropylene or materials available under the trademarks Lexan, Aclar, Cellophane, Mylar and Saran. A preferred support film material is polyester, having the properties of being optically clear, flexible to same degree, non-toxic to bacteria and readily coatible. The support films are preferably flat, relatively thin (e.g. about 5-30 mils thick, preferably disc-shaped, and of appropriate size to fit into the satellite testing chambers with sufficient peripheral separation to permit free flow of the liquid sample 70 to fill the satellite chambers 11.

While the discs 60 are specifically disclosed herein with reference to the diagnostic device of the invention, it will be appreciated by those skilled in the art that them may be incorporated into other devices of similar nature. It will further be appreciated that, while the support films are preferably disc-shaped, the shape is not critical, and they may take other shapes, e.g. oval, square etc., for utilization in other similar devices or for other purposes.

The surfaces of the support films may be pre-treated, for example, to render them hydrophobic or hydrophilic in accordance with procedures conventional in the art, and/or simply to insure that the substrate or other diagnostic material will properly adhere thereto.

The test substances to be coated onto the surface of the support films are preferably incorporated into solutions or suspensions of suitable film-forming polymeric materials. In most instances a water-soluble or water-dispersible film is utilized. It is particularly important, however, that the film-forming materials be compatible with the microorganisms to be identified and the substrates or reagents to be utilized. As example, the film-forming substance used, like the support material itself, should not be antimicrobial, bacteriostatic or interact with the diagnostic substances. Suitable water-soluble film-forming agents may include, as example, modified cellulosic substances, such as methylcellulose, hydroxypropylcellulose, hydroxypropylmethylcellulose, sodium carboxymethylcellulose, and the like, polyvinyl alcohol, polyvinyl pyrolidone, gelatin, dextran and the like. In those instances where a water-insoluble film is desired, suitable film-forming agents would include, for example, nitrocellulose, ethylcellulose, cellulose acetate phthalate, and the like.

The solutions or suspensions of the desired reagents or substrates and the film-forming agents utilized to coat the support films can be prepared in any desired concentration, taking into consideration the nature of the contemplated reactions, the amount of sample material which is likely to be available, the size of the satellite chambers etc. Conveniently, such coating substances would contain from about 0.001 percent by weight to about sixty-five percent by weight of the reagent and/or substrate and from about three percent by weight to about sixty-five percent by weight of the film-forming agent. Higher concentrations of the reagent and/or substrate may be achieved by multiple applications of the coating solution.

Where it is desired to conduct a single test with reagents and/or substrates which may be incompatible with one another, the support films of the invention are particularly advantageous in that such incompatible substances may be coated on opposite sides of the support, thus avoiding contact between the incompatible substances until the determination is actually being conducted.

Of course, a single surface of a support may contain more than one reagent or substrate, for example a combination of materials including a color indicator. The film coating on the supports may additionally contain conventional adjunct materials, such as substances to adjust pH and osmotic pressure, buffers and the like.

Typically, a support film in accordance with the invention could be coated with the following composition:
Side A:
  Dextrose: 32 g
  Polyvinyl alcohol: 8 g
  Suitable buffer, pH 8.0: 1 ml
  Solution of 1 N sodium hydroxide in distilled water, pH 8.0 q.s.: 100 ml
Side B:
  Peptone: 2 g
  Polyvinyl alcohol: 8 g
  Beef extract: 0.2 g Brom cresol purple: 0.2 g
Solution of 1 N sodium hydroxide in distilled water, pH 8.0 q.s.: 100 ml The solutions in this example may be coated onto the respective sides of the support film to concentrations, per 6 mm diameter disc, of 3.4472 mg dextrose, 0.2154 mg peptone, 0.0215 mg beef extract and 0.0215 mg brom cresol purple. Upon reconstitution of the coatings on the support, with 9.2 ml of distilled water or sample in a satellite testing chamber, the concentration of the reactants in the chamber would be equivalent to 17.24 mg/ml dextrose, 1.08 mg/ml peptone, 0.11 mg/ml beef extract and 0.11 mg/ml brom cresol purple.

The media support coated as described above could be employed to determine if a particular organism being tested has the capability to utilize glucose. In order to make such a determination, suspension of the organism in sufficient water or saline to give an optical density of 0.02–0.3 at 640 nm can be utilized. This represents about one colony in 3 ml water. A 0.2 ml sample of this suspension can be reacted with the disc 60 in a suitable receptacle, such as a satellite testing chamber. The sample and disc are then incubated for a suitable time, e.g. 2–4 hours, at 35¼ C. with mild shaking. If the organism has the capability to utilize glucose, the medium will undergo a color change from blue or purple to yellow.

Similar determinations may be conducted utilizing reagents recognized in the art for other carbohydrates, such as arabinose, lactose, sorbitol, maltose, sucrose, xylose, fractose, mannitol, inulin, inositol, ducitol and the like. These skilled in the art appreciate that the ratio of various ingredients such as those discussed above may require some adjustment in order to optimize the determination for a particular carbohydrate. The skilled artisan will likewise appreciate that other indicators recognized in the art may be utilized in place of brom cresol purple. Suitable indicators include, for example, brom phenol, brom cresol green, brom thymol blue, phenol red, cresol red, thymol blue, resazurin and various salts of tetrazolium. This approach is not restricted to measuring the utilization of carbohydrates or reactions involving a shift in pH but may be employed to measure other metabolic activities, enzymes or substrate utilizations. Typical substrates would thus include, for example, citrate, acetate, urea, esculin, nitrate, tartrate, malonate, phenylalanine, lysine, arginine or ornithine.

As an alternative method of diagnostic determination, a media disc 60 in accordance with the invention could be coated with the following composition:
Side A:
  L-lysine: 5.0 g
  Dextrose: 0.05 g
  Polyvinyl alcohol: 10.0 g
  Water: 100 ml
Side B:
  Peptone: 2.0 g
  Beef extract: 0.2 g
  Brom cresol purple: 0.2 g
  Polyvinyl alcohol: 10.0 g
  1 N Hydrochloric acid to adjust pH to 6.5-distilled water q.s.: 100 ml The basic determination discussed above may also be utilized to quantitatively measure the minimum inhibitory concentration (M.I.C9 required for an antibiotic or antibacterial agent against a specific organism. Dics 60 containing varying concentrations of such agent in weight per unit area would be utilized to determine M.I.C. by, for example, application to a gel containing a growing organism. In this method one could rapidly determine the lowest concentration of such agent producing a zone of inhibition. This particular aspect of the disclosed discs 60 may be more applicable to the discs being placed on a plate or suitable support surface rather than incorporation thereof into the diagnostic device of the invention. Antibiotics suitable for incorporation into discs 60 for M.I.C. testing include, for example, ampicillin, amoxycillin, erythromycin, gentamycin, oxytetracycline, tetracycline and the like.

In accordance with the invention, it is possible to identify various groups of microorganisms to the genus and/or species level. Organisms for which this methodology would be particularly applicable would include, for example, Exterobacteriaceae, non-fermentative grain negative rods, grain positive aerobes and anaerobes, yeasts and the like. Those skilled in the art will appreciate that the group of organisms to be identified would determine the tests to be utilized and that by judicious selection of tests one can minimize the number of tests required to obtain maximum separation of groups or pairs of organisms.

For example, tests suitable for identification of members of the family Enterobacteriaceae would include:
  glucose utilization
  ornithine decarboxylase
  citrate utilization
  $H_2S$ production
  phenylalanine deaminase
  lysine decarboxylase
  adonitol utilization
  urea hydrolysis
  arabinose utilization
  arginine dihydrolase
  tartrate utilization
  lactose utilization
  dulcitol utilization
  inositol utilization
  maltose utilization
  esculin hydrolysis
  indole formation
  reduction of nitrates
  production of acetylmethyl carbinol
  production of indole Tests suitable for the identification of non-fermentative gram negative rods would include:
  glucose oxidation
  $H_2S$ production
  arginine dihydrolase
  nitrate utilization
  lysine decarboxylase
  indole production
  sucrose utilization
  xylose utilization
  fructose utilization
  maltose utilization
  cetrimide utilization
  acetamide sensitivity
  urea hydrolysis
  citrate utilization Tests suitable for the identification of medically important yeast would include:
  glucose assimilation
  galactose assimilation
  xylose assimilation
  sucrose assimilation
  trehalose assimilation maltose assimilation
melobiose assimilation
inositol assimilation
raffinose assimilation
cellobiose assimilation
KNO₃ assimilation
urea hydrolysis
citrate utilization Tests suitable for the identification of gram positive bacteria of medical importance would include:
glucose oxidation
nitrate reduction
urea hydrolysis
citrate utilization
o-nitrophenyl-B-D-galactosidase
maltose utilization
xylose utilization
arabinose utilization
sorbitol utilization
esculin utilization
sucrose utilization
sensitivity to detergents
sensitivity to bacitracin
sensitivity to ethyl violet or azide
arginine dihydrolase A possible test sequence for screening for urinary tract infections would include:
lactic dehydrogenase
sensitivity to crystal violet
sensitivity to nalidixic acid
sensitivity of azide
sensitivity to ethyl violet
sensitivity to acetamide
formation of indole from tryptophane
citrate utilization
urea hydrolysis
phenylalanine deaminase
nitrate reduction
sensitivity to ampicillin
sensitivity to gantrisn
sensitivity to tetracycline
sensitivity to kanamycin
sensitivity to carbenicillin By way of a further specific example, the following pertains to tryptophane as a substrate which, as indicated in the above, is useful inter alia in connection with urinary tract infections. In this example the tryptophane substrate is utilized to determine which bacteria in the urine under analysis possess the enzyme indole-tryptophanase, which is able to metabolize tryptophane to produce indole as an end product.

The tryptophane substrate may be prepared in final disc 60 form according to the following.

The required ingredients are given in the following table.

| Item | Ingredient | Amount |
|---|---|---|
| 1 | Trypticase peptone | 15.0 g |
| 2 | Gelvatol (polyvinyl alcohol) | 10.0 g |
| 3 | Purified water | 100.0 ml |
| 4 | .1N Sodium hydroxide | QS to pH 7.0 ± .1 |
| 5 | .1N Hydrochloric acid | |

The tryptophane substrate may be prepared as provided in the following example procedure.

1. In a suitable fleaker dissolve item (1) Trypticase Peptone in item (3) Purified Water.
2. Add and dispense item (2) Gelvatol, mixing at high speed.
3. Place the fleaker in an autoclave and set it on slow exhaust setting. Allow the temperature to reach 180 C. and shut the autoclave off.
4. Leave the autoclave closed for approximately forty-five minutes.
5. Remove the fleaker and mix thoroughly.
6. Adjust the pH to 7.0±0.1 with item (4) 0.1 N NaOH and item (5) 0.1 N HCl.
7. Allow to stand overnight or until all bubbles are equilibrated out of solution.
8. Cast on side A of polyester disc film at 30 mils. Dry.
9. Cast on side B of polyester film at 30 mils. Dry.
10. Punch ¼" discs.

A first disc 60, prepared as above, may thus be utilized in the devices described herein, e.g. in analysis chamber II.

Because of the properties of indole, e.g. colorless, etc, which would normally require expensible or involved techniques for its detection in small amounts, a mechanism is desirable to render the indole readily detectable without the need for expensive equipement or complicated procedures.

To this end use may be made of Kovacs' indole detection system. Because indole is votatile the indicator or reagent may be prepared as a separate disc 63 and placed in the venting chamber 24 above analysis chamber 11 (FIG. 7). This solves the problem also of having to maintain the incompatible substances existing in this example as will be further appreciated in the following.

Kovacs' system involves the use of Kovacs' reagent or indicator which is composed of the following ingredients.

| Ingredient | Amount |
|---|---|
| Pure amyl or isoamyl alcohol | 150 ml |
| p-dimethylaminobenzaldehyde | 10 g |
| concentrated pure Hydrochloric acid | 50 ml |

A prepared film, Kovacs' film, is also needed in this system to create this second disc 63. Kavacs' film is composed of the following thoroughly mixed ingredients.

Nitrocellulose mix: 16 parts
Kovacs' reagent: 1 part

The procedure for generating the discs 63 of indole indicator via Kovacs' system can be as follows.

1. Saturate a piece of lens paper in Kovacs' reagent.
2. Dry the paper.
3. Dip the reagent-impregnated paper in the nitrocellulose film mixture.
4. Dry.
5. Cast into Mylar ® film (e.g.400M 654 polester film).
6. Cast on regenerated cellulose.

This latter step is required as a suitable barrier to prevent interaction of the ingredients of disc 63 with that of Trypophane disc 60 (i.e. the regenerated cellulose overcoating of disc 63 is impervious to the ingredients comprising this second disc). Nevertheless, this overcoating is permeable, as is desired, to the indole generated from the initial test or reaction involving first disc 60.

An alternative approach to the Kovacs system which may be utilized in connection with this Tryptophane example to render the generated indole readily detectable is the so-called Gilles system, which involves an ethelcellulose indole detection film. The material to be provided on disc 63 is comprised of the following ingredients.

| Item | Ingredient | Amount |
|---|---|---|
| 1 | p-dimethylaminobenzaldehyde | 5.0 g |
| 2 | Methanol (absolute) | 50.0 ml |
| 3 | O—phosphoric acid | 10.0 ml |
| 4 | Ethocellulose 20 | 4.0 g |

The procedure for generating such an indole detection disc may be as follows.

Procedure

1. Dissolve Item (1) benzaldehyde and (3) O-phosphoric acid in Item (2) methyl alcohol.
2. Add and dissolve item (4) Ethocel.
3. Cast on Mylar 400M 654.

Alternative overcoatings or barriers which may be used in connection with the Kovacs and Gilles systems to "isolate" until needed the detecting agent(s) or substance(s) which are incompatible with the initial tryptophase enxymatic reaction are:

1. Krylon spray (e.g. 2 coats)
2. Nitro cellulose film

The latter may be prepared by dissolving
 (a) cellulose substrate: 10%
 (b) diethyl phthalale: 5%
in a solvent solution consisting of:
1. alcohol: 5 parts
2. ethyl acetate: 20 parts
3. butyl acetate: 15 parts
4. toluene: 35 parts In each of these overcoating examples, the Kovacs or Gilles detecting agents are prevented from contaminating the initial tryptophane solution that contains the bacteria via a chemical barrier that is water impermeable but indole permeable. A barrier is thus conveniently provided for those diagnostic substances of the disc 60 which are incompatible (e.g. inhibitory) with the enzymatic activity sought, such as where there could otherwise result a pH shift of the reagent that could lead to enough of a change in the substrate to give rise to a false negative result. It is emphasized that such overcoatings are inert, in that they are not reacted with or affect the desired reaction(s) in any way, and are able to carry out their barrier function even where the potential inhibitory substances may actually be one or more of the components of the disc support material itself. It is emphasized also, however, that the disc support material should be compatible with the film forming substance utilized, as otherwise the combination may cause one or more substances to be generated which could adversely affect the reaction(s) intended to take place. It is principally due to the within-indicated restrictions that the search for suitable disc support materials, involving several hundreds of tested support materials, has uncovered only two acceptable substances: Mylar ® (polyester) and Petra ® (polyethylene terephthalate).

The discs 60 described herein are advantageous in a number of particulars. First, they provide analytical media in a dry, stable form which does not require special handling or storage such as refrigeration. Second, they permit rapid determination by either manual or automated methodology without the need to prepare or handle reagents, since the discs contain reagents in pre-measured quantities. Third, they provide a means whereby potentially incompatible reagents are prevented from interacting until the determination is actually to be carried out. Also, they are adaptable to a wide variety of determinations and equally adaptable to micro-analytical procedures.

It will further be appreciated by those skilled in the art that the unique discs 60 of the invention in conjunction with the disclosed device provides means for complete screening and determination programs which can be conducted rapidly and yet with minimal manipulation and no external equipment required. Of course, with the utilization of automated interpretative means, programmed microbiological analysis of a wide range of chemical, biochemical, and immunological determinations can be even more readily carried out. The fact that the disclosed device does not require external means and equipment, such as positive or negative pressurization or centrifuge means, for its utilization, is advantageous in that it may be utilized in many varied clinical environments where such equipment might not be available or could not be afforded. Thus, for example, the devices could be innoculated in a clinical laboratory or a physician's office and then be shipped to a central laboratory where the results would be read and interpreted by automated equipment. The convenience and practical advantage of such a system will be clearly apparent to the skilled artisan.

Discs 60 could be substituted by media pellets. Such pellets could be substantially spherical and comprise at least one substrate or other useful diagnostic substance or layers of the same or different substances. For example, incompatible media, reagents or substrates could be combined by first forming a small pellet of one substance, applying an inert, dissolvable and optically transparent coating acting as a buffer or barrier, and then coating the buffer with the second substance. Additionally one could start with an inert, non-dissolvable, optically transparent core material e.g. of the same material as discs 60, with the various layers then coated thereon.

In connection with these pellets, projections 14 (e.g. FIG. 3) may be replaced by a recess or recesses in the floor of the satellite chamber, to house the pellets.

We claim:

1. A diagnostic device having a first chamber for receiving a sample and a multiplicity of separate analysis chambers in controlled communication only with the first chamber, wherein the improvement comprises the combination of:
   (a) at least one diagnostically useful substance predispensed in solid form to each of the individually viewable, optically transparent analysis chambers;
   (b) optically transparent and flat cover seal means being disposed above each of the analysis chambers to render each analysis chamber individually viewable in a vertical orientation from above said analysis chamber;
   (c) self-contained means for controlling communication between the first source chamber and the optically transparent analysis chambers, and for dispensing sample from the first chamber simultaneously and in uniform amount to each of the analysis chambers concurrently with venting said first chamber said means being adjustably interdisposed between said first chamber and said analysis chambers; and (d) analysis chambers circumferentially arranged relative to the first chamber, each of said analysis chambers sharing in common a wall with the immediately adjacent analysis chambers.

2. A device according to claim 1 wherein said diagnostically useful substance is disposed apart from a wall defining said analysis chamber.

3. A device according to claim 1 or 2 wherein said at least one diagnostically useful substance comprises a pair of such substances which are normally incompatible.

4. A device according to claim 1 or 2 wherein said diagnostically useful substance is coated onto at least one surface of an optically transparent support.

5. A device according to claim 4 wherein at least one diagnostically useful substance is coated onto each side of said support, and at least one of said substances on the one side of said support is normally incompatible with at least one of said substances on the other side of said support.

6. A device according to claim 5 wherein each substance coated onto said support has a property for microorganism identification.

7. A device according to claim 5 wherein said analysis locations are provided with means for supporting a side of said optically transparent support thereby enabling simultaneous access of the sample to all surfaces of said predispensed substances.

8. A device according to claim 1 wherein the optically transparent analysis chambers are circumferentially arranged relative to the first chamber and share in common an optically transparent cover seal means.

9. A device according to claim 1 wherein said self-contained accessing means is adjustably interdisposed between said source and analysis locations and is structured for a reversible linear vertical movement relative to source and analysis locations whereby communication between said source and analysis locations and venting above said source location is concurrently controlled.

10. A device according to claim 9 wherein said self-contained accessing means is a substantially cylindrical sleeve disposed adjacent to and surrounding said source location and structured to provide a vertical displacement.

11. A device according to claim 1 wherein said self-contained accessing means is adjustably interdisposed between said source and analysis locations and is structured for a reversible rotary movement relative to source and analysis locations whereby communication between said source and analysis locations and venting above said source location is concurrently controlled.

12. A device according to claim 11 wherein said self-contained accessing means is a substantially cylindrical sleeve disposed adjacent to and surrounding said source location and structured to provide a horizontal rotary movement.

13. A device according to claim 1 wherein said self-contained accessing means is adjustably interdisposed between said source and analysis locations and is structured for a reversible screw movement whereby communication between said source and analysis locations and venting above said source location is concurrently controlled.

14. A device according to any of claims 13 wherein said self-contained accessing means provides means for simultaneously closing the vent means above the first chamber and blocking communication between the source and analysis locations thereby sealing the dispensed sample at each of the analysis locations.

15. A device according to any of claims 9, 13 or 14 wherein said self-contained accessing means comprises a substantially cylindrical sleeve disposed adjacent to and surrounding said source location.

16. A device according to claim 15 wherein said source location comprises a first chamber and said analysis locations comprise a multiplicity of separate, optically transparent analysis chambers circumferentially spaced about the substantially cylindrical sleeve and source chamber.

17. A device according to claim 16 further comprising a multiplicity of passageway means for facilitating transfer of sample from the first chamber to the optically transparent analysis chambers when said sleeve is moved, said multiplicity of passageway means being formed on the wall defining the first chamber and radiating out to the analysis chambers from said first chamber and each said passageway means being in communication with a an optically transparent, separate analysis chamber.

18. A device according to claim 16 wherein each of the analysis locations includes a venting arrangement above the analysis locations.

19. A device according to claim 18 wherein said venting arrangement includes a venting chamber.

20. A device according to claim 19 wherein said venting arrangement further includes means for enabling the venting chamber to communicate with the respective analysis chamber and the atmosphere.

21. A device according to claim 20 wherein said enabling means is structured to pass gaseous matter and block passage of liquid and solid matter.

22. A device according to claim 19 wherein said venting chamber is disposed above the analysis chamber.

23. A device according to claim 19 wherein said venting chamber is provided with at least one predispensed substance useful in sample identification.

24. A device according to claim 1 wherein said self-contained accessing means comprises a piston arrangement adjustably disposed at the source location for pressurizing the first chamber whereby communication between the source and analysis locations is controlled.

25. A device according to claim 24 wherein said self-contained accessing means further comprises a screw movement adjustable, threaded piston arrangement.

26. A device according to claim 1 further including a multiplicity of inclined passageway means in controlled communication with the source location and the analysis locations for facilitating the dispensing of sample to the analysis locations.

27. A device according to claim 1 wherein a plurality of said substances is predispensed in at least one analysis location.

28. A device according to any one of claims 1, and 27 wherein said substances are in solid form.

29. A device according to claim 28 wherein said substances are coated on opposite sides of a support material which is optically transparent.

30. A device according to claim 29 wherein at least one analysis location is provided with a plurality of said coated supports.

31. Diagnostic method comprising:
(a) predepositing in solid form at least one selected substance useful in the identification of at least a part of a sample, into each of a series of separate, optically transparent analysis chambers;
(b) depositing a sample in a single source chamber;
(c) providing a portion of said sample simultaneously to each of the separate analysis chambers and while maintaining the orientation of the device concurrently venting said source chamber, such that a substantially uniform amount of sample is received therein; and
(d) individually measuring the nature and extent of reactions between the sample portion and substance useful in its identification in each optically transparent, separate analysis chamber whereby the nature and extent of said reactions are indicative of identifying characteristics of said sample.

32. A method according to claim 31 wherein said sample identification comprises identifying microorganisms.

33. A method according to claim 32 wherein said microorganism identification includes measuring the endogenous respiration.

* * * * *